(12) United States Patent
Guha et al.

(10) Patent No.: US 9,782,441 B2
(45) Date of Patent: Oct. 10, 2017

(54) STROMAL CELL THERAPY IN TREATMENT OF RADIATION INJURY

(75) Inventors: Chandan Guha, Scarsdale, NY (US); Subhrajit Saha, Bronx, NY (US); Alan A. Alfieri, Garden City, NY (US); Payel Bhanja, Bronx, NY (US)

(73) Assignee: Albert Einstein College of Medicine, Inc., Bronx, New York ( * ) Notice: Subject to any disclaimer, the term of this patent is extended or adjusted under 35 U.S.C. 154(b) by 176 days.

(21) Appl. No.: 14/131,776

(22) PCT Filed: Jul. 10, 2012

(86) PCT No.: PCT/US2012/046075
§ 371 (c)(1),
(2), (4) Date: Mar. 3, 2014

(87) PCT Pub. No.: WO2013/009753
PCT Pub. Date: Jan. 17, 2013

(65) Prior Publication Data
US 2015/0118206 A1   Apr. 30, 2015

Related U.S. Application Data

(60) Provisional application No. 61/506,385, filed on Jul. 11, 2011.

(51) Int. Cl.
| | | |
|---|---|---|
| *A01N 63/00* | (2006.01) | |
| *A61K 35/12* | (2015.01) | |
| *A61K 35/28* | (2015.01) | |
| *A61K 35/35* | (2015.01) | |
| *C12N 5/077* | (2010.01) | |
| *A61K 35/15* | (2015.01) | |

(52) U.S. Cl.
CPC .............. *A61K 35/28* (2013.01); *A61K 35/15* (2013.01); *A61K 35/35* (2013.01); *C12N 5/0669* (2013.01)

(58) Field of Classification Search
CPC ................................ A01N 63/00; A61K 35/12
See application file for complete search history.

(56) References Cited

U.S. PATENT DOCUMENTS

| | | | | |
|---|---|---|---|---|
| 5,733,542 | A * | 3/1998 | Haynesworth | ............ A61F 2/28 424/422 |
| 2006/0039895 | A1 | 2/2006 | Chute | |
| 2007/0274965 | A1* | 11/2007 | Mitchell | .............. C12N 5/0647 424/93.7 |
| 2009/0035347 | A1 | 2/2009 | Prockop et al. | |
| 2010/0113360 | A1 | 5/2010 | Scadden et al. | |
| 2014/0017209 | A1* | 1/2014 | Aberman | ............... A61K 35/50 424/93.7 |
| 2014/0120065 | A1* | 5/2014 | Zander | ................... A61K 35/28 424/93.7 |

OTHER PUBLICATIONS

Lange et al. (Radiation Rescue: Mesenchymal Stromal Cells Protect from Lethal Irradiation. PLoS One; Jan. 2011; vol. 6(1): 1-12).*
Morishima et al. (The clinical significance of human leukocyte antigen (HLA) allele compatibility in patients receiving a marrow transplant from serologically HLA-A, HLA-B and HLA-DR matched unrelated donors. Blood, 2002 vol. 99(11) 4200-4206).*
Wan et al. (Nonadherent Cell Population of Human Marrow Culture Is a Complementary Source of Mesenchymal Stem Cells (MSCs). Journal of Orthopaedic Research (2006) pp. 21-28).*
The International Search Report dated Feb. 5, 2013 for PCT Application No. PCT/US2012/046075.
The Written Opinion of International Searching Authority dated Feb. 5, 2013 for PCT Application No. PCT/US2012/046075.
Loi et al. "Limited restoration of cystic fibrosis lung epithelium in vivo with adult bone marrow-derived cells." American Journal of Respiratory and Critical Care Medicine, vol. 173 (2006), pp. 171-179.
Haudek et al. "Bone marrow-derived fibroblast precursors mediate ischemic cardiomyopathy in mice." PNAS Nov. 28, 2006, vol. 103:48, pp. 18284-18289.

* cited by examiner

*Primary Examiner* — Scott Long
*Assistant Examiner* — Natalie Moss
(74) *Attorney, Agent, or Firm* — Amster, Rothstein & Ebenstein LLP

(57) ABSTRACT

Methods are provided for treating, mitigating or protecting from radiation-induced injury using bone marrow stromal cells expanded in culture, adipose-tissue derived non-adherent stromal cells, or the culture supernatant thereof.

12 Claims, 25 Drawing Sheets

STROMAL CELL THERAPY IN TREATMENT OF RADIATION INJURY

CROSS-REFERENCE TO RELATED APPLICATIONS

This application is a U.S. national phase of PCT Application No. PCT/US2012/0046075, filed Jul. 10, 2012, which claims benefit of U.S. Provisional Application No. 61/506,385, filed Jul. 11, 2011, the contents of each of which is hereby incorporated by reference.

Throughout this application various publications are referred to by number in square brackets. The disclosures of these publications, as well as of all patents, patent application publications and books referenced herein, are hereby incorporated by reference in their entirety into the subject application to more fully describe the art to which the subject invention pertains.

STATEMENT OF GOVERNMENT SUPPORT

This invention was made with government support under grant numbers 1RC2 AI087612-01 and 1U19AI091175-01 awarded by the National Institute of Allergy and Infectious Diseases. The government has certain rights in the invention.

BACKGROUND OF THE INVENTION

Nuclear accidents and terrorism presents a serious threat for mass casualty. Accidental or intended radiation exposure in a mass casualty setting presents a serious and on-going threat. Acute radiation injury is manifested in organs that have rapidly proliferating cells, such as, intestine, mucosal lining of the body, bone marrow and skin. Manifestation of acute radiation injury includes anemia, bleeding, diarrhea, sepsis, mucosal and cutaneous ulceration and even death due to target organ failure. At radiation doses of 3 to 8 Gy, morbidity and lethality is primarily caused from hematopoietic injury and victims can be rescued by bone marrow transplantation (BMT). However, with exposure to larger doses, victims suffer irreversible hematopoietic and gastrointestinal injury and usually perish despite supportive care and BMT. There are currently no approved treatments to alleviate Acute Radiation Syndrome (ARS) in victims of radiological disaster with anticipated multi-organ failure or to effectively treat/protect first responders from ARS. To date, individuals categorized as H4 (dose and volume irradiation dependent) receive supportive care post-radiation exposure that includes reverse isolation, antibiotics, antivirals, antifungals, platelet and blood transfusions and maintenance of fluid/electrolyte balance prior to bone marrow transplantation (BMT), resulting in only marginal survival. Also, while BMT may have some benefit in mitigating hematopoietic syndrome, currently there are no approved medical countermeasures to alleviate radiation-induced gastrointestinal syndrome (RIGS).

While radioprotective agents can be used with some success when given prior to radiation exposure they are of limited use when used post-exposure. This circumstance motivates the continued search for agents that alleviate radiation damage post-exposure.

Late radiation injury is manifested in organs that have parenchymal cells that divide slowly, such as, brain, spinal cord and liver. In addition, chronic radiation injury can occur in any organ, including lung, kidney, intestine, esophagus, bladder and rectum. Chronic radiation injury is caused by aberrant repair of acute radiation injury and is usually seen as a fibrotic response.

Syndromes and symptoms that are caused by radiation injury include xerostomia (dry mouth), dysphagia (difficulty in swallowing) due to pharyngeal and esophageal strictures, breast fibrosis, cutaneous ulcers, dyspnea due to radiation pneumonitis and lung fibrosis, radiation-induced liver damage, kidney failure due to fibrotic kidneys, rectal bleeding due to radiation proctitis, bladder and urethral injury, diarrhea, enteric bleeding and sepsis due to radiation-induced gastrointestinal syndrome, and anemia, thrombocytopenia and neutropenia from radiation-induced marrow failure. Basically most organs can manifest some form of acute or chronic radiation injury.

There are currently there are no approved medical countermeasures to alleviate radiation-induced gastrointestinal syndrome (RIGS), resulting from direct cytocidal effects on intestinal stem cells (ISC) and crypt stromal cells. RIGS results from a dose-dependent, direct cytocidal and growth inhibitory effects of irradiation on the villous enterocytes, crypt intestinal stem cells (ISC)[1,2,3], the stromal endothelial cells[4] and the intestinal subepithelial myofibroblasts (ISEMF)[5]. Subsequent loss of the mucosal barrier results in microbial infection, septic shock and systemic inflammatory response syndrome. The cells in the ISC niche, consisting of micovascular endothelial cells, mesenchyme-derived ISEMF[5] and pericryptal macrophages[6] provide critical growth factor/signals for ISC regeneration and intestinal homeostasis[7]. Of these, ISEMF continuously migrate upward from the crypt base to the villous tip along with ISC and transit amplifying enterocytes, establishing signaling crosstalk and regulating ISC self-renewal and differentiation [5,8]. ISEMF interacts with pericryptal macrophages with subsequent release of PGE2 that could reduce radiation-induced apoptosis of enterocytes[9,10]. Pericryptal macrophages form synapses with crypt stem cells and secretes growth factors to stimulate ISC proliferation[6] upon activation of Toll-like receptors sensing the entry of bacteria and other intestinal pathogens.

Since RIGS results from a combination of radiation-induced loss of crypt progenitors and stromal cells along with aberrant signaling in the ISC niche, it is possible that the acute loss of stromal cells in the ISC niche would require rapid compensation of their functions. This might possibly be best achieved with cell replacement therapies that restore the ISC niche after irradiation so that the stromal cells can secrete growth factors and provide necessary signals for survival, repair and regeneration of the irradiated intestine. Earlier reports demonstrated that donor bone marrow-derived cells could contribute to multiple lineages in the gastrointestinal tract and facilitate intestinal regeneration in patients with graft-versus-host disease and ulcer[11] and in animal models of colitis[12].

Because of ease in cell culture and its ability to differentiate into multiple tissue lineages, transplantation of bone marrow-derived mesenchymal stem cells (MSC) has been a very attractive option for a wide range of clinical applications[13], such as, severe treatment-resistant graft-versus-host diseases of the gut[14]. Besides trans-differentiating into ISEMF and stimulating ISC proliferation, MSC transplantation has also been shown to reprogram host macrophages to induce an anti-inflammatory response and thereby minimizing sepsis in a murine model of colitis[15]. Intravenous injection of MSC resulted in enhanced engraftment in irradiated organs, including, small intestine with subsequent increase in the regeneration of the intestinal epithelium and accelerated recovery of the villi post-radiation in mice models[16]. Genetic modification of donor MSCs with superoxide dismutase[17] or CXCR4[18]transgene augments the engraftment and mitigation of intestinal radiation injury. However, till date, transplantation of whole bone marrow or MSC has not been successful in ameliorating RIGS and improve survival of mice that received >10 Gy of irradiation in a single fraction[16,17,18].

Effective therapies for treating, mitigating or protecting from or preventing injuries associated with exposure to excessive radiation are still needed, and the present invention provides such therapies.

SUMMARY OF THE INVENTION

A method is provided of treating, mitigating, or protecting from, an injury associated with exposure of a subject to radiation comprising administering to the subject before, during or after exposure of the subject to the radiation an amount of bone marrow-derived stromal cells or an amount of a supernatant obtained from a culture of bone marrow-derived stromal cells, effective to treat, mitigate or protect from an injury associated with exposure of a subject to radiation.

A method is also provided of treating, mitigating, or protecting from, an injury associated with exposure of a subject to radiation comprising administering to the subject before, during or after exposure of the subject to the radiation an amount of adipose tissue-derived non-adherent stromal cells or an amount of a supernatant obtained from a culture of adipose tissue-derived non-adherent stromal cells, effective to treat, mitigate or protect from an injury associated with exposure of a subject to radiation.

Also provided are bone marrow-derived stromal cells expanded in culture, or a supernatant derived from such a culture, for use in protecting from, or mitigating, or treating, a radiation-induced pathology in a subject.

Also provided are adipose tissue-derived non-adherent stromal cells expanded in culture, or a supernatant derived from such a culture, for use in protecting from, or mitigating, or treating, a radiation-induced pathology in a subject.

Also provided is a method of increasing the chance of survival of a subject exposed to an otherwise lethal dose of radiation comprising administering to the subject before, during or after exposure of subject to the otherwise lethal dose of radiation an amount of bone marrow-derived stromal cells or an amount of a supernatant obtained from a culture of bone marrow-derived stromal cells, or an amount of adipose tissue-derived non-adherent stromal cells or an amount of a supernatant obtained from a culture of adipose tissue-derived non-adherent stromal cells, effective to increase the chance of survival of the subject exposed to the otherwise lethal dose of radiation.

Also provided is a method of increasing the survival rate of a plurality of subjects exposed to an otherwise lethal dose of radiation comprising administering to each of the subjects before, during or after exposure of subjects to the otherwise lethal dose of radiation an amount of bone marrow-derived stromal cells or an amount of a supernatant obtained from a culture of bone marrow-derived stromal cells, or an amount of adipose tissue-derived non-adherent stromal cells or an amount of a supernatant obtained from a culture of adipose tissue-derived non-adherent stromal cells, effective to increase the survival rate of a plurality of subjects exposed to the otherwise lethal dose of radiation.

Additional objects of the invention will be apparent from the description which follows.

BRIEF DESCRIPTION OF THE DRAWINGS

FIG. 4(A). Confocal microscopic imaging of EGFP expression in the jejunum of Lgr5-EGFP-ires-CreERT2 transgenic mice. Lgr5-EGFP+ve crypt cells are present at 1 d post-AIR but are absent at 3.5 d post-AIR, indicating the time course of radiation-induced ISC death. BMASCT inhibits the radiation-induced cell loss of Lgr5+ISCs. Confocal microscopic images (63×) were magnified 2.3× (inset). Nucleus was stained with DAPI and pseudo colored with gray. 4(B). Flow cytometric analysis of EGFP expression in crypt cells of Lgr5-EGFP-ires-CreERT2 transgenic mice post-AIR.

DETAILED DESCRIPTION OF THE INVENTION

Abbreviations

Figures 1A, 1B, 1C, 1D, 1E:
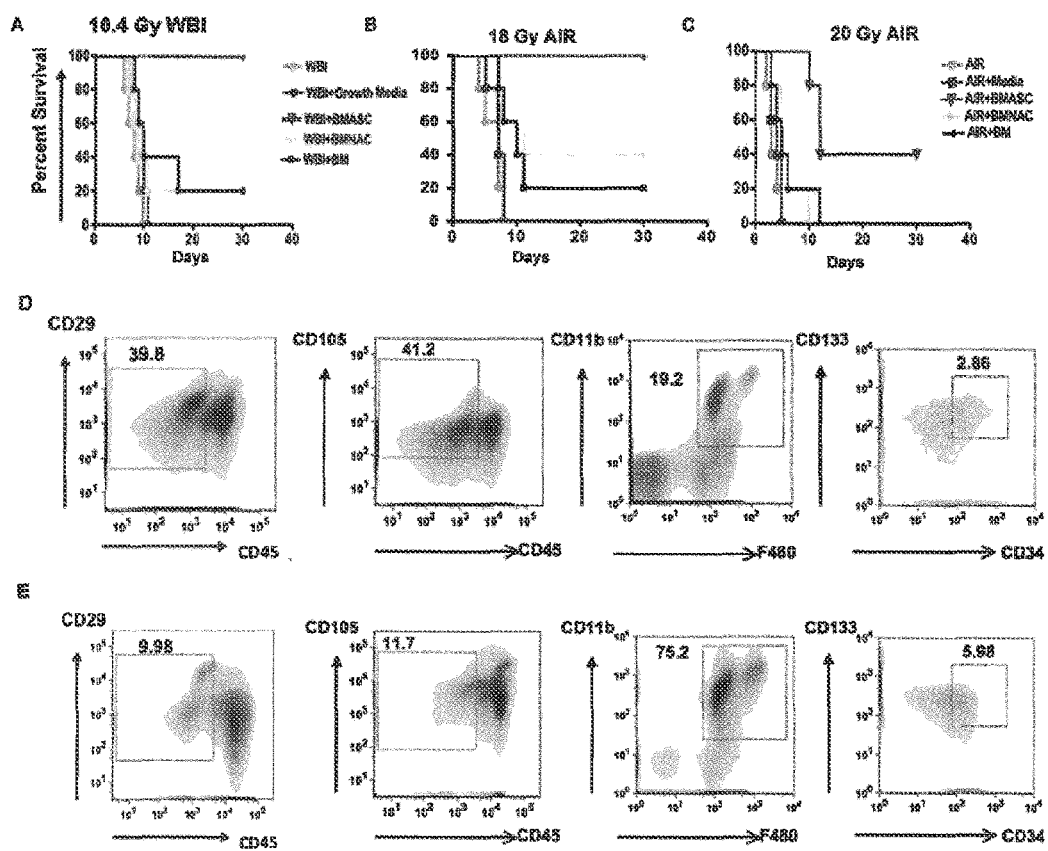
FIG. 1(A)-1(E). BMASCT improves survival of C57Bl/6 mice following AIR. Kaplan-Meier survival analysis of mice (n=25) receiving BMASCT, 24 and 72 hrs after irradiation, showed 100% survival after 1(A) 10.4 Gy WBI (p<0.0006) and 1(B) 18 Gy AIR (p<0.0007); and 40% survival after 1(C) 20 Gy AIR (p<0.01). Whole bone marrow, BMNAC and culture media failed to improve survival. 1(D)-1(E) show flow cytometric characterization. 1(D) BMASC and 1(E) BMNAC population using MSC-specific (CD10S+ CD45−/CD29+CD45−), macrophage-specific (CD11b+ F480+) and endothelial-specific (CD133+CD34+CD45−) markers.
Figures 2A, 2B:
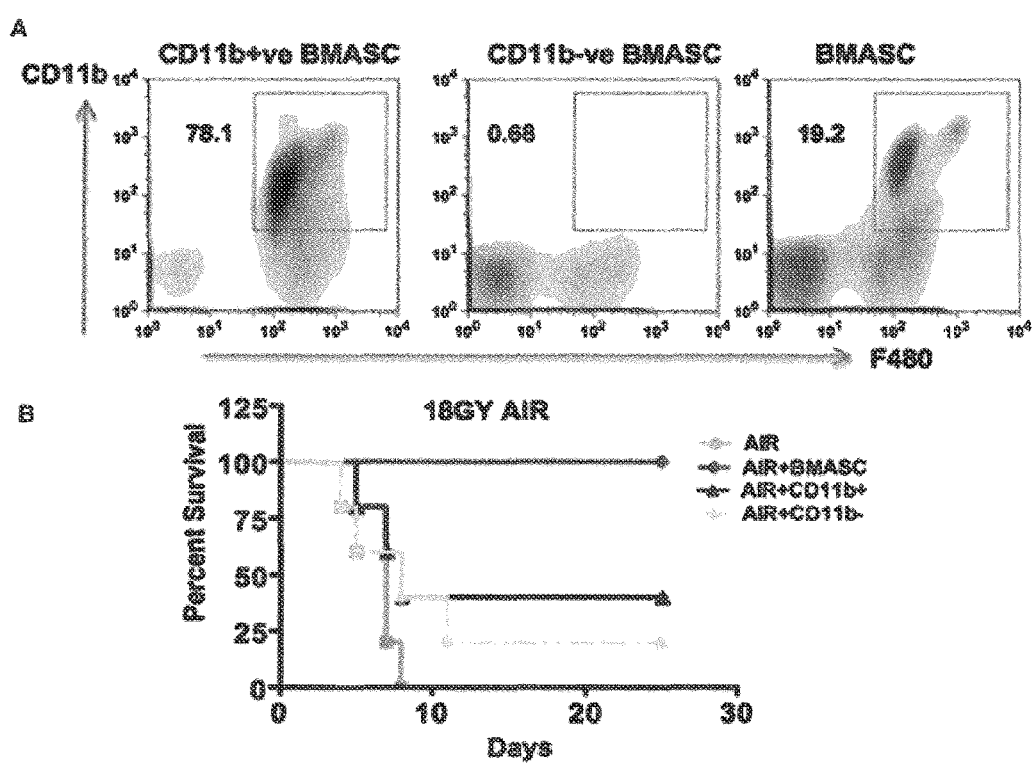
FIG. 2(A)-2(B). Both myeloid and non-myeloid fractions of BMASC are needed for RIGS mitigation. 2(A). Flow cytometry of macrophage population in CD11b+ and CD11b− BMASC. 2(B). Kaplan-Meier survival analysis.

AIR Abdominal Irradiation
bFGF basic Fibroblast Growth Factor
BMT Bone marrow transplantation
BMASC Bone marrow-derived adherent stromal cell
BMASCT Bone marrow-derived adherent stromal cell transplantation
BMNAC Bone marrow-derived non-adherent cell
CSF Colony Stimulating Factor
CXCL12 Chemokine (C-X-C motif) ligand 12

DPPIV-ve Dipeptidyl peptidase-deficient mice (C57Bl/6 background)
EGF Epidermal Growth Factor
FGF Fibroblast Growth Factor
EGFP Enhanced Green Fluorescent Protein
IGF1 Insulin-like Growth Factor 1
ISC Intestinal Stem Cell
ISEMF Intestinal subepithelial myofibroblasts
KGF Keratinocyte growth factor
MSC Mesenchymal Stem cells
PDGFb Platelet derived growth factor-b
RIGS Radiation-induced Gastrointestinal Syndrome
α-SMA α-Smooth Muscle Actin
VEGF Vascular Endothelial Growth Factor
WBI Whole Body Irradiation As used herein, an "injury associated with" exposure of a subject to radiation is an injury, pathology or disease symptom or disease state in a subject understood in the art to be caused by exposure of the subject to excessive radiation. Examples include, but are not limited to, radiation-induced gastrointestinal syndrome, radiation-induced pulmonary syndrome, radiation-induced bone marrow syndrome, radiation-induced bladder injury, radiation-induced liver damage, radiation-induced salivary gland injury, radiation-induced kidney injury, radiation-induced proctitis, radiation-induced esophagitis, radiation-induced cutaneous ulcer, radiation-induced fibrosis, radiation-induced pharyngeal dysfunction, radiation-induced mucosal ulcer and/or fistula, or a radiation-induced injury resulting from exposure to nuclear radiation.

As used herein, "protection" from an injury associated with exposure to radiation means an intervention before exposure to radiation which prevents, or which reduces, radiation injury or one or more symptoms thereof.

As used herein, "mitigation" of an injury associated with exposure to radiation means an intervention after radiation exposure but before induction or manifestation of clinical symptoms from the injury which reduces the injury or one or more symptoms thereof as compared to the extent of the injury or severity of symptom which usually occurs without the intervention.

As used herein, "treatment" of an injury associated with exposure to radiation means an intervention after radiation exposure and appearance of clinical symptoms of the injury which reduces, ameliorates or stabilizes the injury or one or more symptoms thereof.

In an embodiment, bone marrow-derived stromal cells or the adipose tissue-derived non-adherent stromal cells are isolated. In an embodiment, the culture supernatant of bone marrow-derived stromal cells is isolated. In an embodiment, the culture supernatant of adipose tissue-derived non-adherent stromal cells is isolated.

The bone marrow-derived stromal cells (whether expanded in culture or not), adipose tissue-derived non-adherent stromal cells (whether expanded in culture or not), or the culture supernatant of either or both thereof can be administered by any method known in the art including parentally, enterally or topically. In non-limiting embodiments the administration is by transfusion, subcutaneously, intravenously, by infusion, orally, topically, or via an osmotic pump. In non-limiting embodiments, administration can be directly into the site of the disease or injury, e.g. injection into a radiation-damaged organ or tissue, or locally, or can be systemic.

In an embodiment of the methods described herein involving administering a supernatant, the methods can be performed, mutatis mutandis, with culture media, preferably sterilized, conditioned from contact of the media with cultured bone marrow-derived stromal cells or with cultured adipose tissue-derived non-adherent stromal cells.

The bone marrow-derived stromal cells (whether expanded or not in culture), adipose tissue-derived non-adherent stromal cells (whether expanded or not in culture), or the culture supernatant of either or both referred to herein can be administered to the subject in a pharmaceutical composition comprising a pharmaceutically acceptable carrier. As used herein, a "pharmaceutically acceptable carrier" is a pharmaceutically acceptable suspending vehicle or medium suitable for delivering the cells or supernatants to the animal or human subject. Such carriers are well-known in the art. The carrier is selected with the planned manner of administration in mind.

Examples of acceptable pharmaceutical carriers include those compatible with the health or viability of the administered cells, or supernatant, and include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, subcutaneous administration, intravenous administration, transdermal administration, intranasal administration, infusion and administration through an osmotic mini-pump.

The treatments described herein may be a component of a combination therapy or an adjunct therapy, i.e. the subject or patient in need of the treatment is also given another treatment or drug for the disease in conjunction with one or more of the instant treatments. This combination therapy can be sequential therapy where the patient is treated first with one treatment and then the other drug, or the two are given simultaneously. These can be administered independently by the same route or by two or more different routes of administration depending on the dosage forms employed.

A method is provided of treating, mitigating, or protecting from, an injury associated with exposure of a subject to radiation comprising administering to the subject before, during or after exposure of the subject to the radiation an amount of bone marrow-derived stromal cells or an amount of a supernatant obtained from a culture of bone marrow-derived stromal cells, effective to treat, mitigate or protect from an injury associated with exposure of a subject to radiation.

A method is also provided of treating, mitigating, or protecting from, an injury associated with exposure of a subject to radiation comprising administering to the subject before, during or after exposure of the subject to the radiation an amount of adipose tissue-derived non-adherent stromal cells or an amount of a supernatant obtained from a culture of adipose tissue-derived non-adherent stromal cells, effective to treat, mitigate or protect from an injury associated with exposure of a subject to radiation.

Also provided is a method of increasing the chance of survival of a subject exposed to an otherwise lethal dose of radiation comprising administering to the subject before, during or after exposure of subject to the otherwise lethal dose of radiation an amount of bone marrow-derived stromal cells or an amount of a supernatant obtained from a culture of bone marrow-derived stromal cells, or an amount of adipose tissue-derived non-adherent stromal cells or an amount of a supernatant obtained from a culture of adipose tissue-derived non-adherent stromal cells, effective to increase the chance of survival of the subject exposed to the otherwise lethal dose of radiation.

Also provided is a method of increasing the survival rate of a plurality of subjects exposed to an otherwise lethal dose of radiation comprising administering to each of the subjects before, during or after exposure of subjects to the otherwise lethal dose of radiation an amount of bone marrow-derived stromal cells or an amount of a supernatant obtained from a culture of bone marrow-derived stromal cells, or an amount of adipose tissue-derived non-adherent stromal cells or an amount of a supernatant obtained from a culture of adipose tissue-derived non-adherent stromal cells, effective to increase the survival rate of a plurality of subjects exposed to the otherwise lethal dose of radiation.

In an embodiment of the methods described herein regarding exposure to radiation, the radiation is gamma radiation.

In an embodiment of the methods described herein regarding exposure to radiation, the radiation is 1-3 Gy, 3-5 Gy, 5-7 Gy, 7-10 Gy or greater than 10 Gy.

In an embodiment of the methods described herein, the injury associated with exposure of the subject to radiation is radiation-induced gastrointestinal syndrome, radiation-induced pulmonary syndrome, radiation-induced bone marrow syndrome, radiation-induced bladder injury, radiation-induced liver damage, radiation-induced salivary gland injury, radiation-induced kidney injury, radiation-induced proctitis, radiation-induced esophagitis, radiation-induced cutaneous ulcer, radiation-induced fibrosis, radiation-induced pharyngeal dysfunction, radiation-induced mucosal ulcer and/or fistula, or a radiation-induced injury resulting from exposure to nuclear radiation.

In an embodiment of the methods described herein, the bone marrow-derived stromal cells are administered. In an embodiment of the methods, the supernatant is administered. In an embodiment of the methods, the bone marrow-derived stromal cells are, or the supernatant is, administered by infusion into the subject.

In an embodiment of the methods described herein, the bone marrow-derived stromal cells are obtained from the subject prior to the subject being exposed to the radiation.

In an embodiment of the methods described herein, the bone marrow-derived stromal cells are human leukocyte antigen-matched (HLA-matched) to the HLA type of the subject.

In an embodiment of the methods described herein, the bone marrow-derived stromal cells are, or the supernatant obtained from a culture of bone marrow-derived stromal cells is, administered to the subject prior to the exposure of the subject to the radiation. In an embodiment of the methods described herein, the bone marrow-derived stromal cells are, or the supernatant obtained from a culture of bone marrow-derived stromal cells is, administered to the subject subsequent to the exposure of the subject to the radiation.

In an embodiment of the methods described herein, the bone marrow-derived stromal cells are administered, and have been expanded in number by growing them in culture prior to administration to the subject.

In an embodiment of the methods described herein, the bone marrow-derived stromal cells have been grown in culture conditions comprising a basal medium.

In an embodiment of the methods described herein, the adipose tissue-derived non-adherent stromal cells are administered. In an embodiment of the methods described herein, the supernatant is administered. In an embodiment of the methods described herein, the adipose tissue-derived non-adherent stromal cells are, or the supernatant is, administered by infusion into the subject.

In an embodiment of the methods described herein, the adipose tissue-derived non-adherent stromal cells are obtained from the subject prior to the subject being exposed to the radiation.

In an embodiment of the methods described herein, the adipose tissue-derived non-adherent stromal cells are human leukocyte antigen-matched (HLA-matched) to the HLA type of the subject.

In an embodiment of the methods described herein, the adipose tissue-derived non-adherent stromal cells are, or the supernatant obtained from a culture of adipose tissue-derived non-adherent stromal cells is, administered to the subject prior to the exposure of the subject to the radiation.

In an embodiment of the methods described herein, the adipose tissue-derived non-adherent stromal cells are, or the supernatant obtained from a culture of adipose tissue-derived non-adherent stromal cells is, administered to the subject subsequent to the exposure of the subject to the radiation.

In an embodiment of the methods described herein, the adipose tissue-derived non-adherent stromal cells have been amplified in number by growing them in culture prior to administration to the subject. In an embodiment of the methods described herein, the adipose tissue-derived non-adherent stromal cells have been grown in culture conditions comprising a basal medium.

In an embodiment of the methods described herein, the method further comprises culturing the bone marrow-derived stromal cells prior to administering them to the subject.

In an embodiment of the methods described herein, the method further comprises obtaining the bone marrow-derived stromal cells from the subject prior to administering them to the subject.

In an embodiment of the methods described herein, the method further comprises culturing the adipose tissue-derived non-adherent stromal cells prior to administering them to the subject.

In an embodiment of the methods described herein, the method further comprises obtaining the adipose tissue-derived non-adherent stromal cells from the subject prior to administering them to the subject.

In an embodiment of the methods described herein, the method further comprises administering CD11b+ F480+ macrophages to the subject.

In an embodiment of the methods described herein, the bone marrow-derived stromal cells comprise CD133+ CD34+ CD45− endothelial progenitor cells. In an embodiment of the methods, the bone marrow-derived stromal cells comprise CD45+ hematopoietic cells.

In an embodiment of the methods described herein, the bone marrow-derived stromal cells comprise bone marrow-derived adherent stromal cells.

In an embodiment of the methods described herein, the adipose tissue-derived non-adherent stromal cells comprise CD133+ CD34+ Flk+ endothelial progenitor cells. In an embodiment of the methods described herein, the adipose tissue-derived non-adherent stromal cells comprise CD105+ CD45− mesenchymal stem cells.

In an embodiment of the methods described herein, the subject is exposed to 3-10 Gy of radiation.

In an embodiment of the methods described herein, the subject is exposed to in excess of 10 Gy of radiation.

In an embodiment of the methods described herein, the cells or supernatant are administered to the subject less than 72 hours after exposure to the radiation.

In an embodiment of the methods described herein, the cells or supernatant are administered to the subject after 24 hours after the beginning of exposure to the radiation, but less than 72 hours after the beginning of exposure to the radiation. In an embodiment, the cells or supernatant are administered to the subject 24 hours after the end of exposure to the radiation, but less than 72 hours after the end of exposure to the radiation.

Also provided are bone marrow-derived stromal cells expanded in culture, or a supernatant derived from such a culture, for use in protecting from, or mitigating, or treating, a radiation-induced pathology in a subject. In an embodiment, the bone marrow-derived stromal cells are isolated. Also provided are adipose tissue-derived non-adherent stromal cells expanded in culture, or a supernatant derived from such a culture, for use in protecting from, or mitigating, or treating, a radiation-induced pathology in a subject. In an embodiment, the adipose tissue-derived non-adherent stromal cells are isolated. All of the various embodiments listed for the methods above are also applicable to the bone marrow-derived stromal cells expanded in culture, or a supernatant derived from such a culture, for use in protecting from, or mitigating, or treating, a radiation-induced pathology in a subject. All of the various embodiments listed for the methods above are also applicable to the adipose tissue-derived non-adherent stromal cells expanded in culture, or a supernatant derived from such a culture, for use in protecting from, or mitigating, or treating, a radiation-induced pathology in a subject.

In accordance with the methods of the present invention, the subject is a mammal. Preferably, the subject is a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

1. Bone Marrow-Derived Stromal Cells

BMASCT mitigates RIGS and improves survival of mice after otherwise lethal doses of irradiation. Mortality from acute radiation syndromes results from dose-dependent radiation injury to various organs. While BMT is effective in improving survival of mice exposed to doses up to 8-9 Gy, it is relatively ineffective as the sole treatment with higher doses of exposure. This laboratory has previously demonstrated that a whole body exposure of >10.4 Gy induces RIGS and 100% mortality within 10-15 days in C57Bl/6 mice[1]. In order to confirm that RIGS is induced after exposure to a single fraction of WBI of 10.4 Gy, we examined whether BMT can improve the survival of C57Bl/6 mice. While 100% of the untreated animals died within 10 days, animals receiving BMT had only 20% survival (FIG. 1A), indicating that whole marrow that contained primarily CD45+ve hematopoietic cells (FIG. 10(A)-10(D)) failed to rescue these animals from RIGS. It was subsequently examined whether transplantation of bone marrow-derived stromal cells that have been enriched for MSC, EPC and macrophages upon culture in mesenchymal basal medium could mitigate radiation injury in these animals. FIG. 1(A) demonstrates that BMASCT rescued 100% of the irradiated animals, indicating that stromal cell therapy may provide factors to repair and regenerate the intestinal epithelium damaged by irradiation.

Figure 11A:
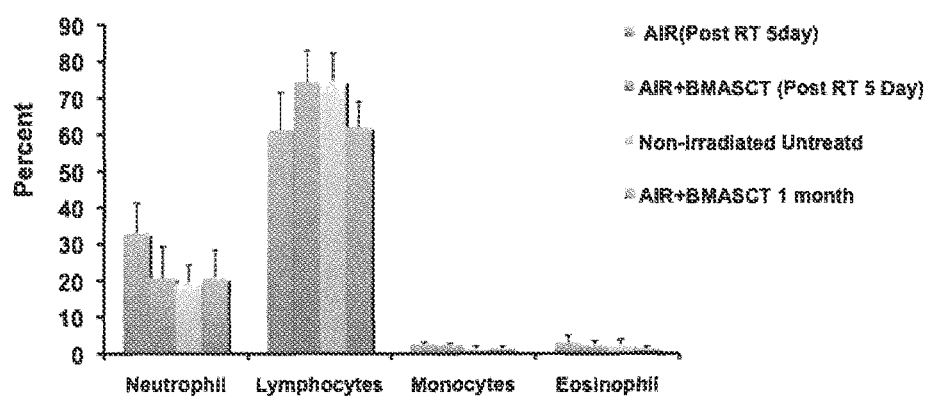
FIG. 11(A)-(B). Blood count was performed with the help of Antech Diagnostics (Lake Success, N.Y.) to evaluate the effect of abdominal irradiation (AIR) on hematopoesis. Absence of any significant changes in (A) differential count and (B) number of RBC and among the irradiated and transplanted group in comparison to untreated control group suggested AIR could not affect the bone marrow.
Figure 11B:
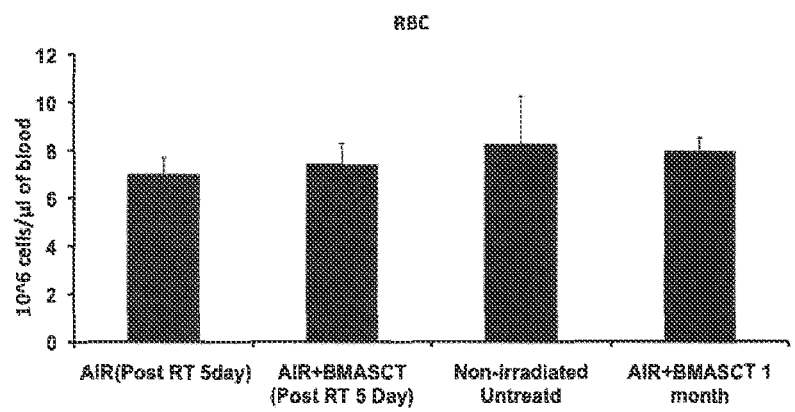

To limit the exposure of the bone marrow to irradiation while escalating the dose to intestine, AIR was delivered (12-20 Gy) after shielding the thorax, head and neck and extremities, as described previously [19,20]. AIR did not significantly impact the peripheral blood count at day 5 (FIG. 11(A)-(B)) post-exposure, indicating that the bone marrow was not severely damaged by AIR. Control animals that received either, PBS, or culture medium died within 10 days after exposure to AIR>16 Gy with characteristic signs and symptoms of RIGS, including, diarrhea, black stools and weight loss. In contrast, animals that received AIR+BMASCT had well-formed stools, maintained body weight (24.1±0.7 g in AIR+BMASCT versus 16.21±1.8 g in AIR cohort, p<0.001) and had 100% survival beyond 25 days (18 Gy AIR, p<0.0007, FIG. 1(B)). At 20 Gy, BMASCT rescued 40% of the animals with survival greater than 25 days, while irradiated animals without BMASCT died within 5 days (median survival time of AIR cohort, 3±0.5 d versus AIR+BMASCT cohort, 12±1.8 d; p<0.01, FIG. 1(C)). Transplantation of CD45+ hematopoietic cell-enriched bone marrow derived non-adherent cell (BMNAC) and whole bone marrow cells failed to rescue AIR-treated mice (FIG. 1(B)-1(C), 1(E) & FIG. 10(A)-(D)), indicating that stromal cells were responsible for the salvage of RIGS.

Figure 12:
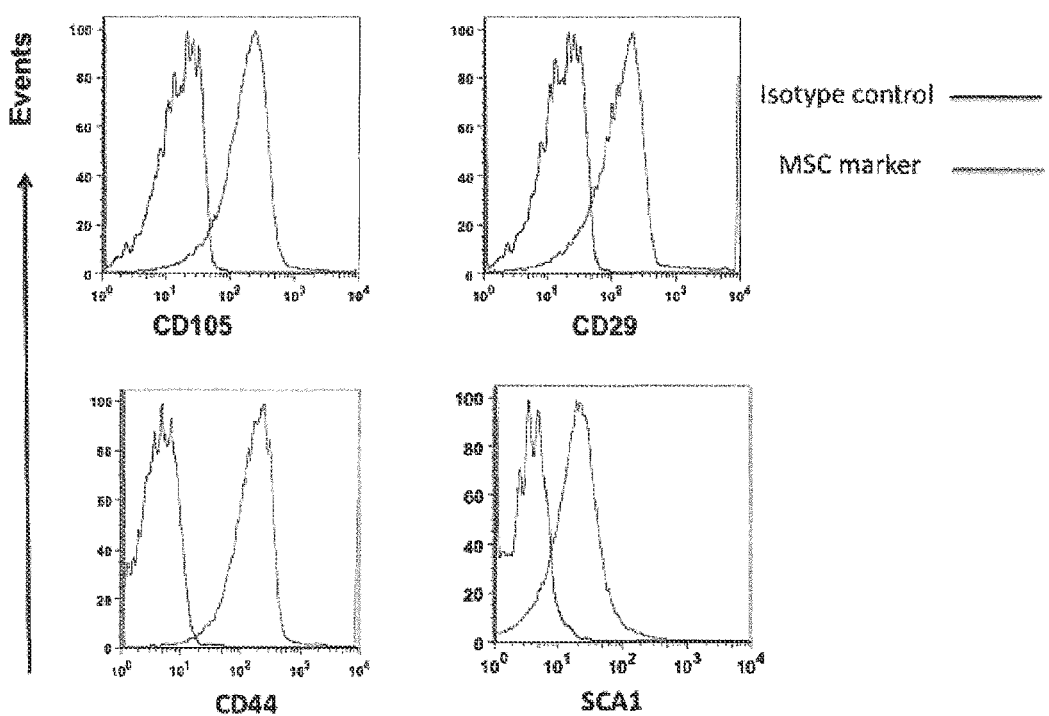
FIG. 12. Expression of different MSC surface markers CD105, CD29, CD44, SCA1 in BMASC population. Staining for IgG isotype fluorescence was used as a control. Isotype control for CD105, CD29, CD44 and SCA-1 are rat IgG2a, hamster IgG, rat IgG2bK and rat IgG2aK respectively.
Figure 13:
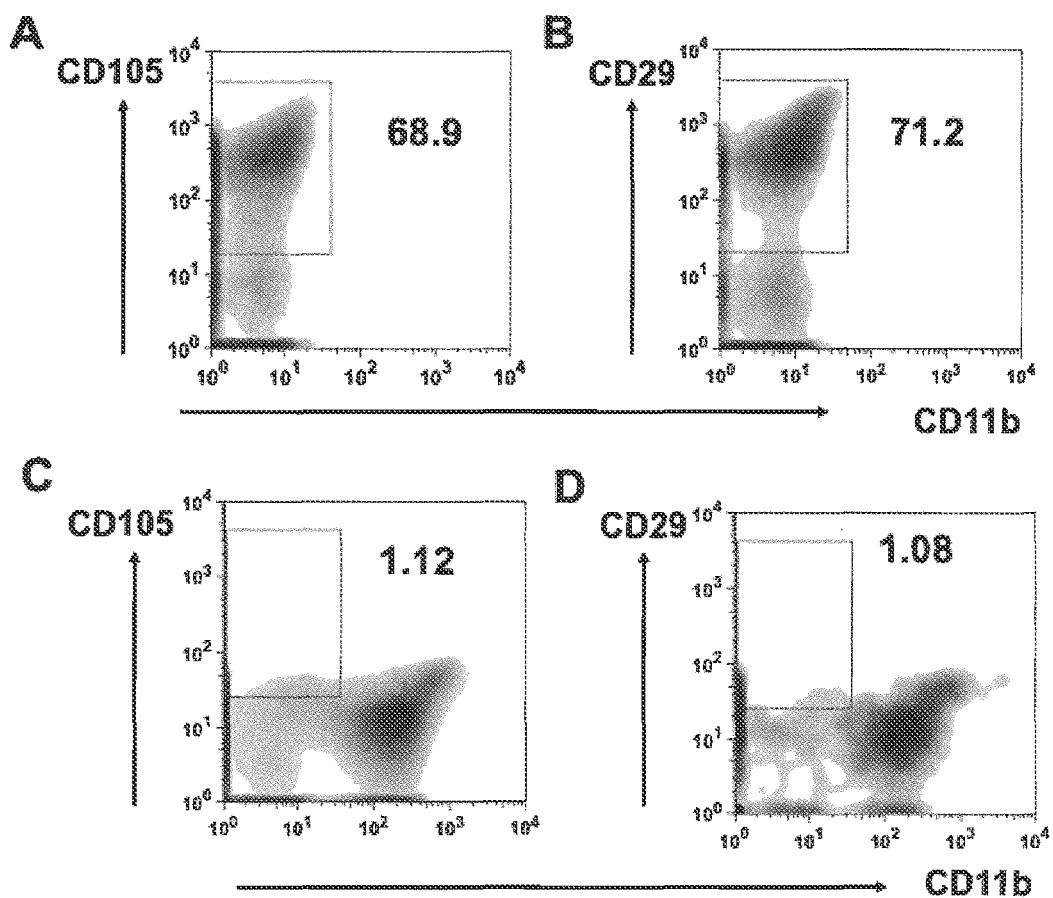
FIG. 13(A)-(D). Flowcytometric characterization of CD11b−ve (A-B) and CD11b+ve (C-D) BMASC population for CD105 and CD29 (MSC marker) expression. It was noted that CD11b−ve BMASC population was primarily enriched with CD105 and CD29 positive cells.

Both myeloid and non-myeloid cell populations are needed for RIGS mitigation. Flow cytometric analysis of donor cells demonstrated that BMASC population included, primarily MSCs (CD105+CD45− 41.2%±1.8; CD29+CD45− 39.8%+1.2), macrophages (CD11b+F480+ 19.2%±1.2) and endothelial progenitors (CD133+CD34+CD45− 2.6%±0.89) and CD45+ hematopoietic cells (FIG. 1(D)). CD44 and Sca1 staining further confirmed the presence of MSC population (FIG. 12). To evaluate the individual roles of CD11b+ macrophage-enriched cells versus CD11b− MSC-enriched stromal cell fraction (FIG. 13(A)-(D)) in RIGS mitigation, BMASC population was fractionated by cell sorting using anti-CD11b-magnetic beads, followed by transplantation 24 hrs post-AIR. Transplantation of either the macrophage-enriched (78.1%±2.8 F480+ cells), MSC-deficient (<1.5% CD105+ve cells) CD11b+ve BMASC or macrophage-deficient (0.68%±0.03 F480+ cells), MSC-enriched (68-71% CD105+ve) CD11b−ve BMASC cell population mitigated only 30-40% of the animals irradiated with 18 Gy AIR (FIG. 2(A)-2(B), FIG. 13(A)-(D)). Survival was salvaged to 100% when the CD11b+ and CD11b− populations were admixed and transplanted, indicating that the combination of macrophages and bone marrow stromal cells, including MSC and EPC fractions was necessary for RIGS mitigation.

Figures 3A, 3B, 3C:
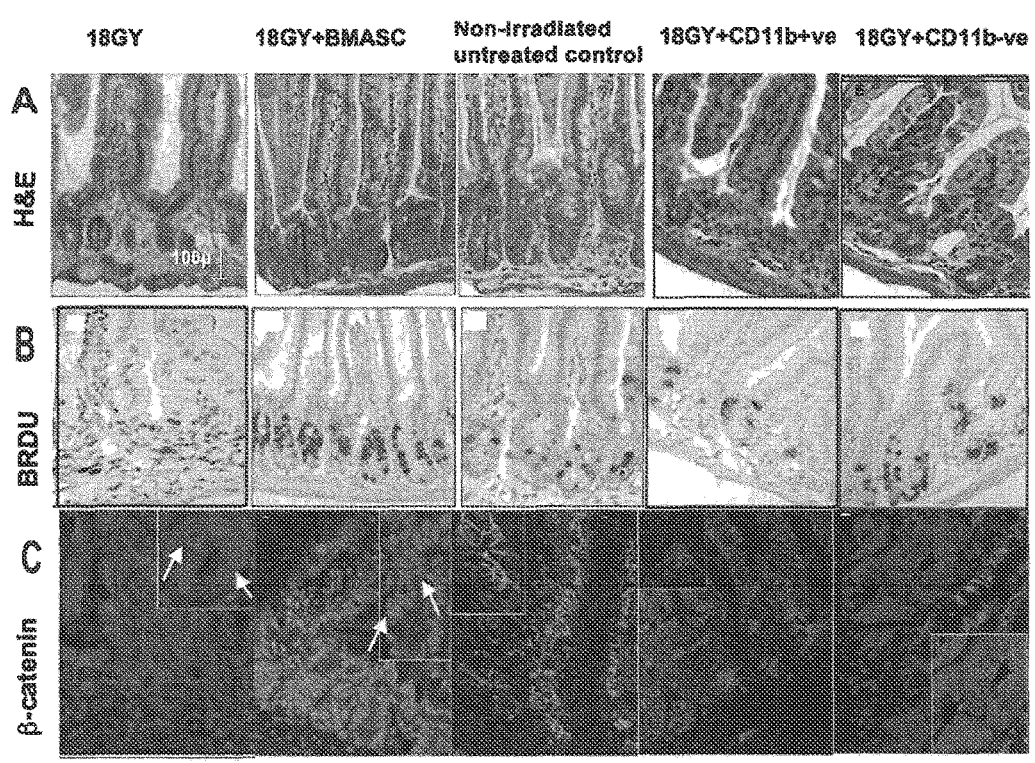
FIG. 3(A)-3(F). BMASCT mitigates RIGS by promoting structural and functional regeneration of the irradiated intestine. 3(A). H&E staining, 3(B). Brdu immunohistochemistry, 3(C). β-catenin immunohistochemistry. β-catenin stained medium gray and nucleus was stained with DAPI (pseudo colored with darkest gray). Confocal microscopic images (63×) were magnified 2.3× (inset). Note the greater crypt depth 3(A), increase in crypt cell proliferation 3(B) and an increase in nuclear translocation of β-catenin (stained lighter gray) in AIR+BMASCT cohort compared to other cohorts. 3(D). Number of regenerative crypts, 3(E). Crypt proliferation rate and 3(F). Xylose absorption assay. A time course study showed significant recovery (p<0.0003) of xylose absorption at 7 days post-irradiation in AIR+ BMASCT-treated animals compared to the AIR cohort.
Figures 3D, 3E:
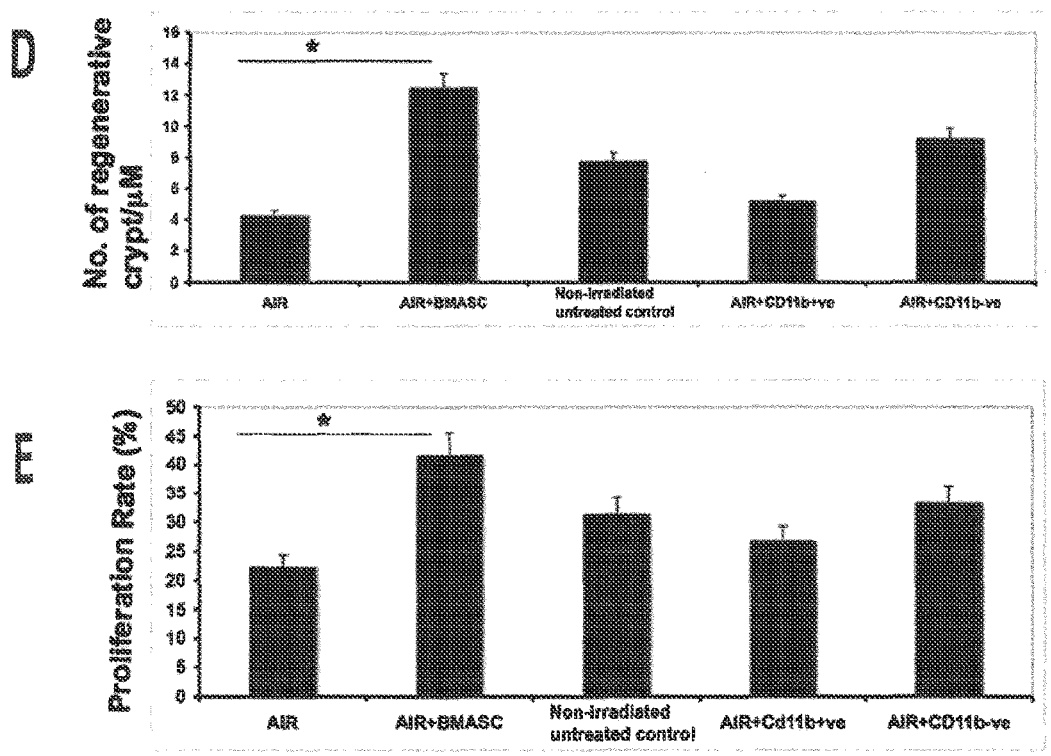
Figure 14:
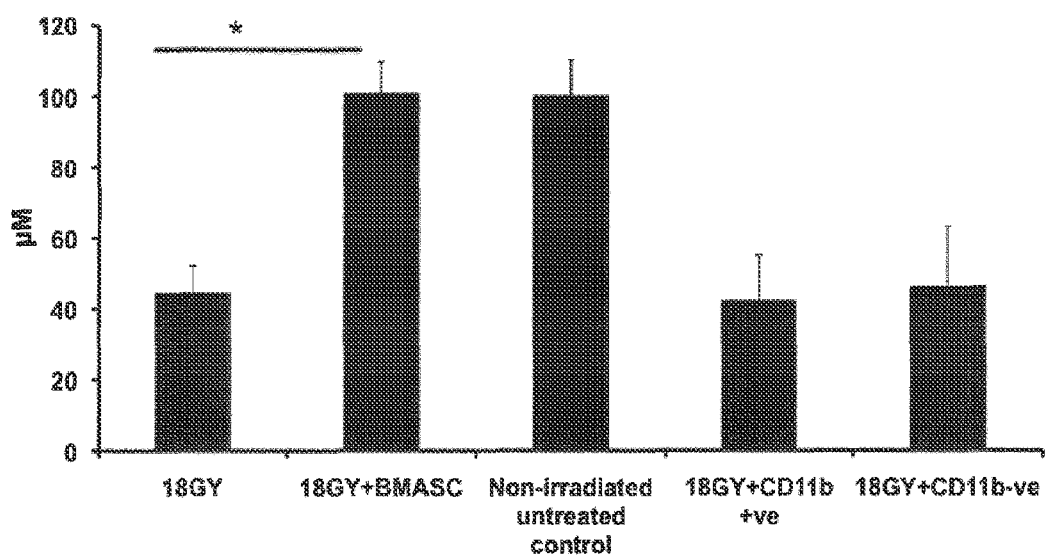
FIG. 14. BMASC transplantation significantly increases crypt depth compared to AIR control.

BMASCT induces structural and functional regeneration of intestine. Histomorphological evaluation after hematoxylin-eosin staining demonstrated that the AIR+BMASCT-treated animals exhibited an increase in the overall size of the crypts and maintained villous length (FIG. 3(A), FIG. 14). The percentage of the BrdU+ve crypt epithelial cells synthesizing DNA was significantly enhanced in this cohort of mice at 3.5 days post-irradiation (AIR+BMASCT, 42.82±2.01 versus AIR, 23.43±1.66; P<0.04; FIGS. 3(B) and 3(E)). The numbers of regenerative crypt microcolonies per unit intestinal cross sectional area at 3.5 days post-irradiation serves as a surrogate indicator of crypt regenerative response post-irradiation[1,21,22]. The crypt microcolony count was increased significantly in AIR+BMASCT cohort, compared with those that received AIR alone (AIR+BMASCT, 12.5+1.2/μm versus AIR, 6.8+0.8, p<0.004, FIG. 3D), indicating intestinal regenerative response following BMASCT. Consistent with the regenerative response, immunohistological analysis demonstrated the presence of nuclear β-catenin in the AIR+BMASCT-treated animals, while cytosolic staining was predominant in the animals receiving AIR (FIG. 3(C)), suggesting that BMASCT activates the Wnt β-catenin pathway in crypt cells to stimulate proliferation post-irradiation.

Figure 3F:
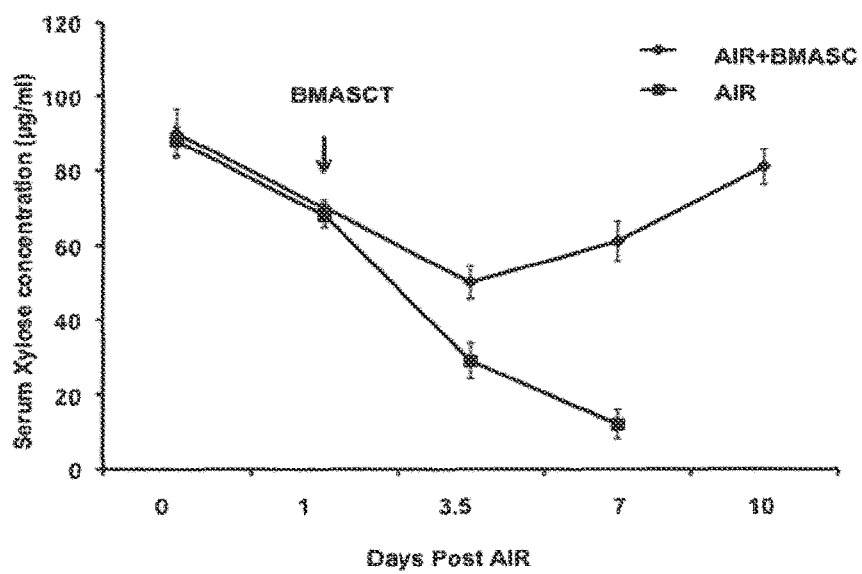

A xylose absorption test was performed to determine the functional recovery of the intestinal villi in RIGS. Since xylose is not metabolized in the body, serum xylose level is a good indicator of the intestinal absorptive capacity in animals fed with a test dose of xylose[1]. Compared to animals that received AIR alone, xylose absorption was significantly improved in animals that received BMASCT at 7 d post AIR (AIR+BMASCT, 72+5.5 g/ml vs. AIR, 35+2.7 g/ml; p<0.004; FIG. 3(F)), indicating quick functional restitution of the intestinal villi.

Figures 4A, 4B:
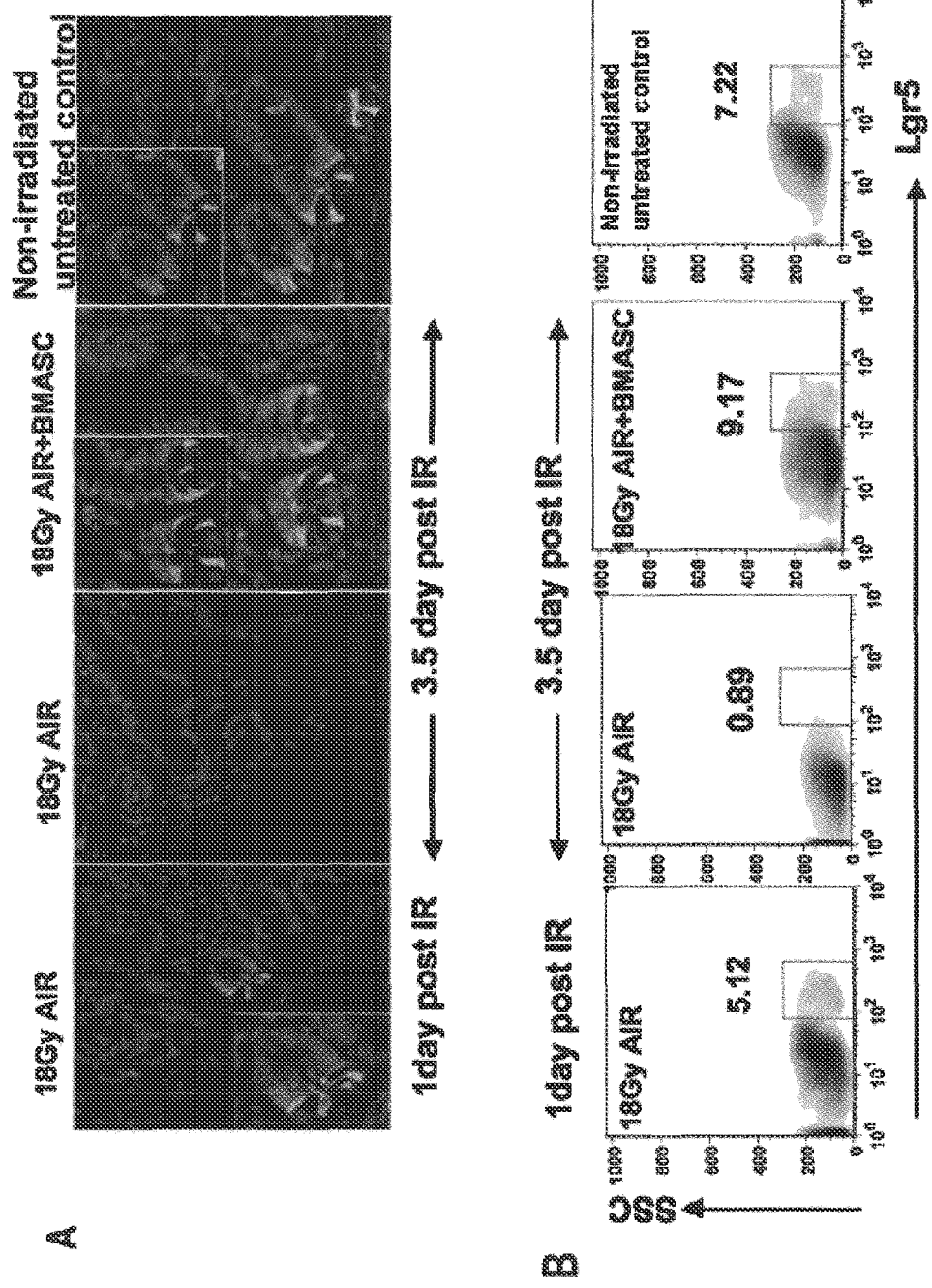
FIG. 4(A)-4(B). BMASCT promotes survival of Lgr5-positive crypt base columnar cells following AIR.
Figure 15:
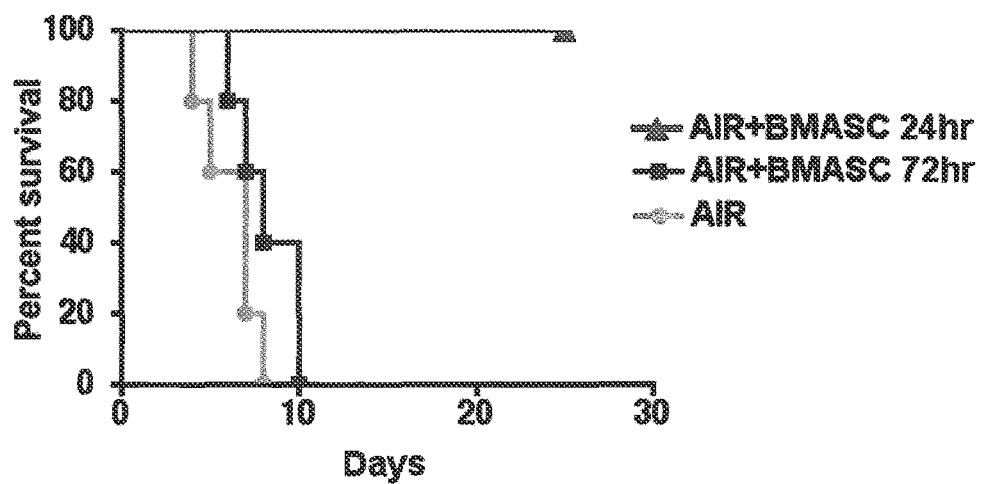
FIG. 15. Kaplan-Meier survival analysis. Mice (n=15) receiving first dose of BMASC at 72 h post AIR followed by second dose failed to mitigate RIGS in contrast to BMASCT at 24 h followed by 72 hr second where 100% survival were noted.
Figure 16:
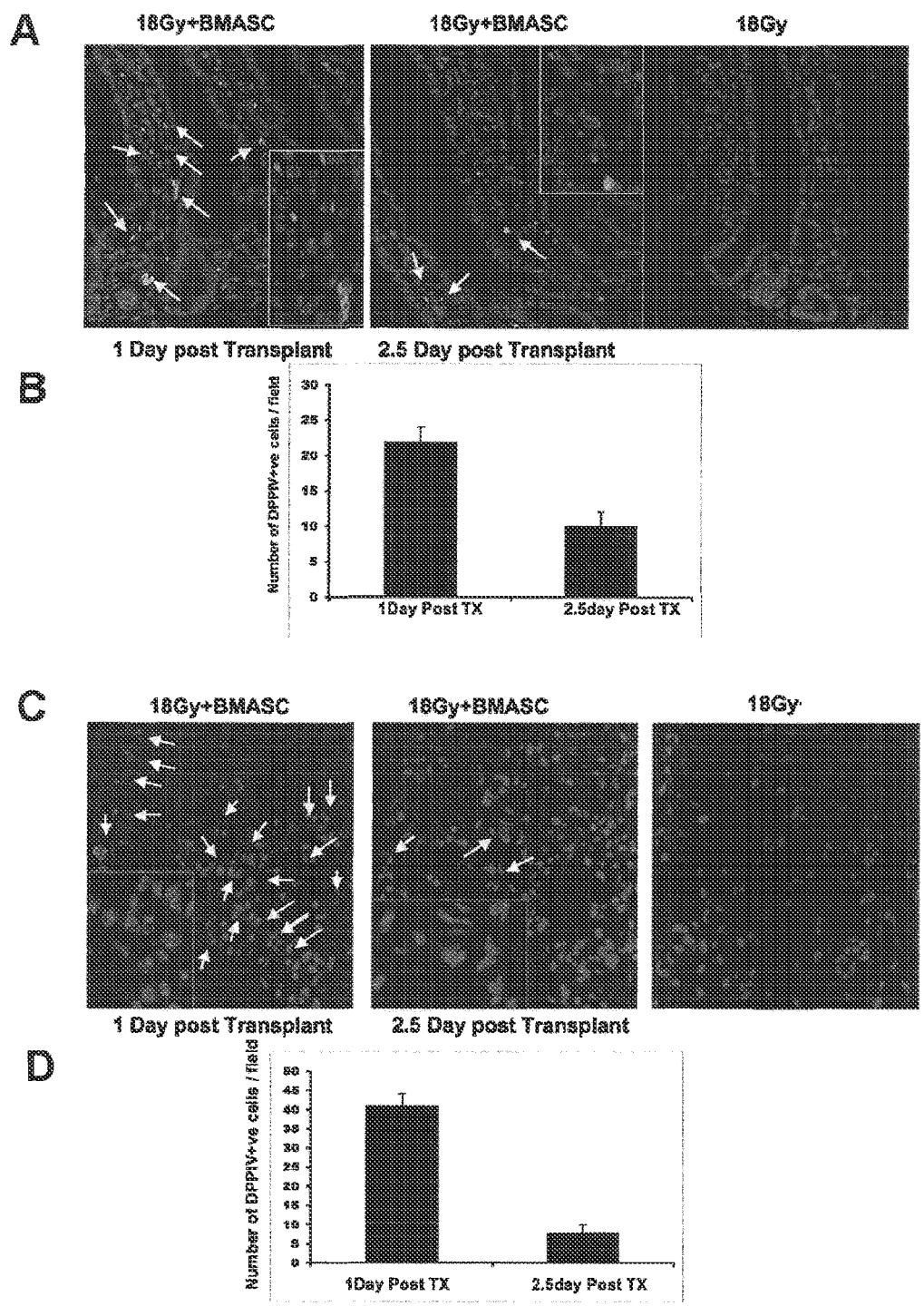
FIG. 16(A)-16(D). Transplanted BMASC were primarily detected in intestine and lung. BMASC from DPPIV positive wild type mice were transplanted to DPPIV negative mice exposed to AIR. (16(A)-16(D)) DPPIV immunohistochemistry followed by confocal microscopic analysis. DPPIV positive BMASC (stained light gray) were found primarily in the lung 16(C) and intestine 16(A). Nucleus was stained with DAPI and pseudo colored with darker gray. Quantification of engrafted DPPIV+ve cells. Significantly higher number of engrafted cells in lung (p<0.002) 16(B) and in intestine (p<0.004) 16(D) was noted at 1 day post AIR compared to 3.5 day post AIR. Confocal microscopic images (63×) were magnified 2.3× and presented in inset. The number of DPPIV positive cells were counted using volocity soft version 5 (Improvision). Based on the intensities, number of cells were determined by scoring at least 10 fields from each animal (n=3). Resolution of the images were same for both experimental and control groups.

BMASCT promotes survival of irradiated Lgr5-positive crypt base columnar cells. The effect of AIR on the number of Lgr5-EGFP+ve crypt base columnar cells was examined, the putative ISC population[3,23], in the jejunum of Lgr5-EGFP-IRES-creERT2 transgenic mice by detecting EGFP expression using confocal microscopy. While these cells are present at 1 d post-AIR, they are absent at 3.5 d post-AIR (FIG. 4(A)). Flow cytometric analysis confirmed the gradual loss of Lgr5+ve crypt ISCs following irradiation exposure (5.17±1.8 at 1 d vs. 0.89%±0.15 at 3.5 d; p<0.001; FIG. 4(B)). In contrast, BMASCT increased the number of Lgr5-EGFP+ve CBCs at 3.5 d post-AIR (FIG. 4(A)). Flow cytometric analysis confirmed that BMASCT increased the number of irradiated Lgr5-GFP+ve crypt cells at 3.5 d post-AIR (9.27%±1.75, vs. 0.89%±0.15; (p<0.0003; FIG. 4(B)), possibly by providing signals for survival and growth. This provides window of radiation mitigation, whereby BMASCT rescued lethally irradiated mice within 24 hrs of irradiation, but not after 72 hrs (FIG. 15).

Figures 5A, 5B:
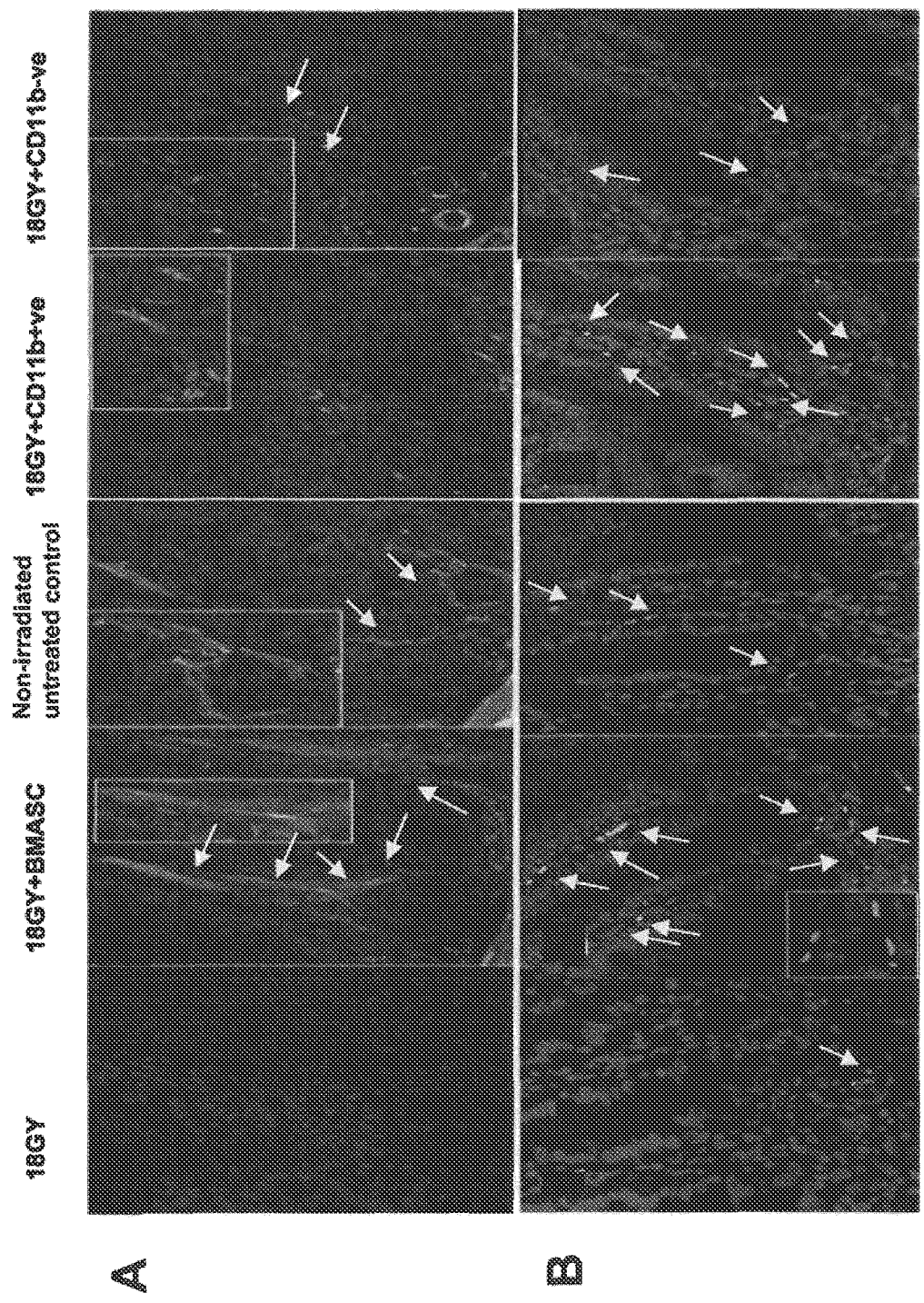
FIG. 5(A)-5(C). BMASCT restores the ISEMF and pericryptal macrophages of the ISC niche, 3.5 days post-AIR. 5(A). ISEMF detection by immunohistochemistry and confocal microscopy using anti-α-SMA (gray, indicated with arrow) and anti-desmin (stained green) antibodies. α-SMA+ ve and desmin-ve ISEMF were reduced in AIR-treated animals, which was restored by BMASCT. Nucleus was stained with DAPI (dark colored). 5(B). F480 Immunhistochemistry and confocal microscopic analysis and 5(C). Quantification of Number of pericryptal macrophages. The number of F480+ve macrophages (white, indicated with arrow) increased at 3.5 d post-AIR in the AIR+BMASCT (p<0.003) and CD11b+ve BMASCT (p<0.006) group, compared to the AIR cohort, respectively. Nucleus was stained with DAPI (pseudo colored with gray). Confocal microscopic images (63×) were magnified 2.3× (inset).
Figure 5C:
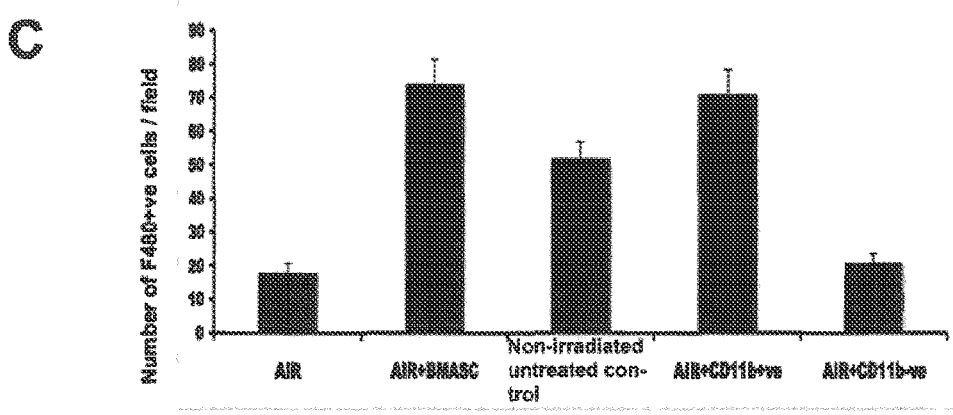

BMASCT restores the ISEMF and pericryptal macrophages in the irradiated ISC niche. ISEMF and pericryptal macrophages provide the epithelial-mesenchymal cross-talk signals for growth, differentiation and cell fate determination to ISCs [6,8,9]. Immunohistochemistry and confocal microscopy demonstrated that 18 Gy AIR reduces the number of α-SMA+, desmin-ve ISEMF (FIG. 5(A)) and F480+ve pericryptal macrophages (FIG. 5(B)). BMASCT restored the α-SMA+, desmin-ISEMF (FIG. 5(A)) and increased the number of pericryptal and subepithelial macrophages in the lamina propria (AIR+BMASCT, 72+6.4/hpf versus AIR, 15+3.2/hpf; p<0.003; FIG. 5(B),(C)) of irradiated mice. Transplantation of the CD11b−ve fraction of BMASC restored the ISEMF population (FIG. 5(A)), whereas transplantation of the CD11b+ve fraction exhibited an increase in the number of intestinal macrophages (p<0.006, FIG. 5(B),(C)), which indicates that transplantation of both CD11b+ and CD11b− fractions restores the ISC niche for RIGS mitigation.

Figure 6A:
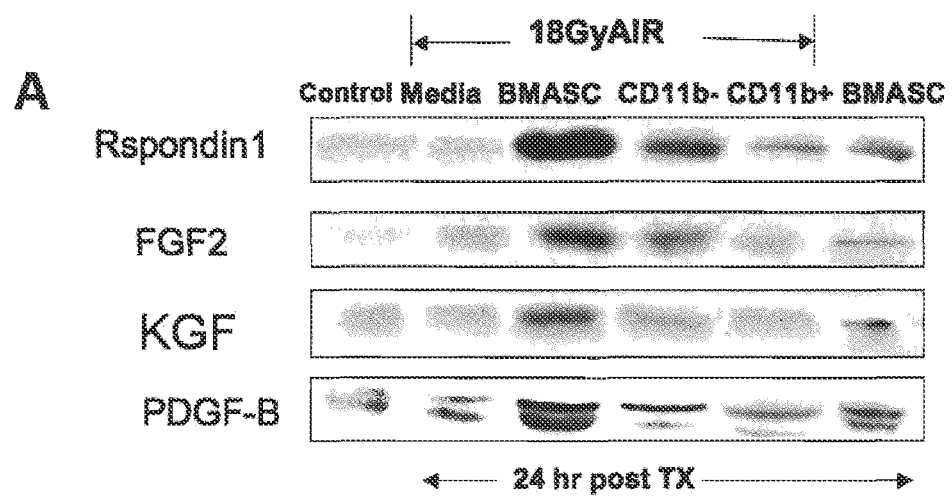
FIG. 6(A)-6(D). Serum analysis of intestinal growth factors and cytokines. 6(A). Immunoblot analysis. An increase in the serum levels of R-spondin1, FGF2, KGF and PDGF-B was noted in AIR+BMASCT cohort compared to AIR. 6(B)-(D). Multi cytokine ELISA. 6(B). Anti-inflammatory cytokines, IL6 (p<0.004) and IL10 (p<0.002) levels were significantly increased in the AIR+BMASCT, cohort compared to AIR alone. 6(C). Pro-inflammatory cytokines, IL12A (p<0.001) and IL17 (p<0.006) levels were induced in AIR cohort, compared to AIR+BMASCT treated animals (IL12A, p<0.001; IL17, p<0.008). 6(D). Myeloid cytokines, GM-CSF (p<0.007) and G-CSF (p<0.006) were increased in AIR+BMASCT group, compared to AIR.
Figure 17:
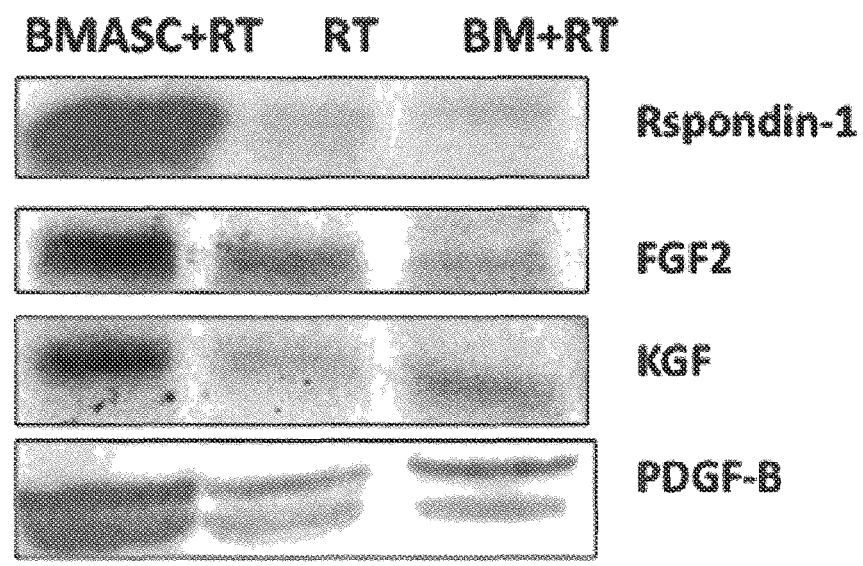
FIG. 17. Immunoblot analysis of intestinal growth factors in serum. An increase in the serum levels of R-spondin1, FGF2, KGF and PDGF-B was noted in AIR+BMAST treated animals, compared to animals that received AIR+BM or AIR alone.

BMASCT induces secretion of intestinal growth factors and anti-inflammatory cytokines. We examined the engraftment and repopulation of the donor cells in various organs by transplanting dipeptidyl peptidase IV (DPPIV)-proficient BMASC in DPPIV-deficient C57Bl/6 host. Although 3-5 DPPIV+ve donor cells were noted per intestinal villi upon DPPIV immunohistochemistry, the majority of the donor cells were lodged in the lungs (FIG. 16(A)-16(D)). It was therefore hypothesized that the regeneration and repair of the irradiated intestine is mediated by paracrine growth factors that were secreted by the donor BMASCs. Immunoblot analysis of the serum of animals that received AIR+BMASCT showed an increase in serum levels of R-spondin1, FGF2, PDGF-B and KGF by 2-8 folds at 24 h post-BMASCT, compared to animals that received AIR alone (FIG. 6(A)). Interestingly, animals that received whole BMT did not show an increase in serum R-spondin1 levels (FIG. 17). While KGF and R-spondin1 can increase the proliferation of intestinal crypt cells[1,24], FGF2 and PDGF-B could support the growth of endothelial cells [4] and ISEMF [25], respectively in the ISC niche of AIR+BMASC-treated animals.

Figures 6B, 6C, 6D:
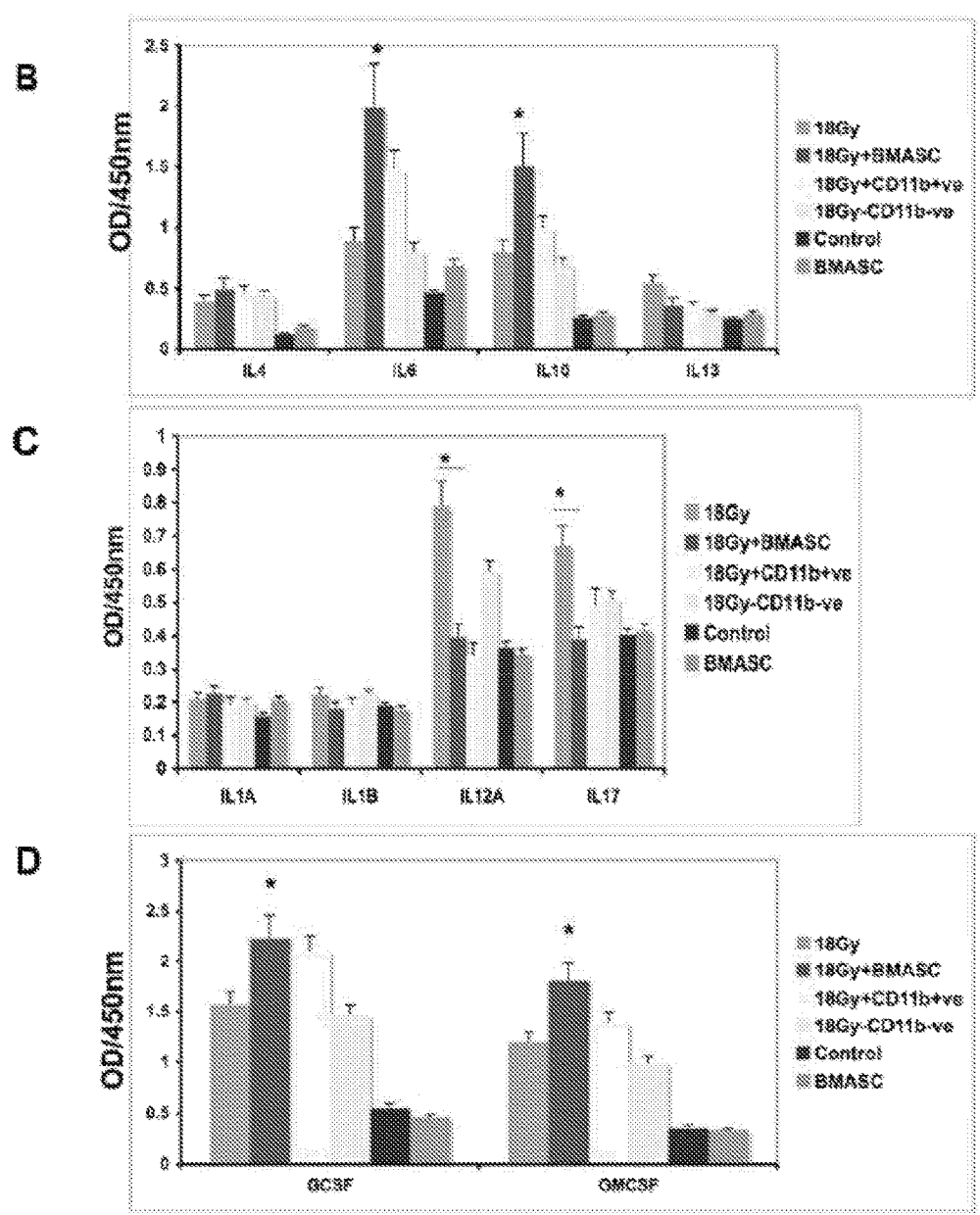
Figure 18:
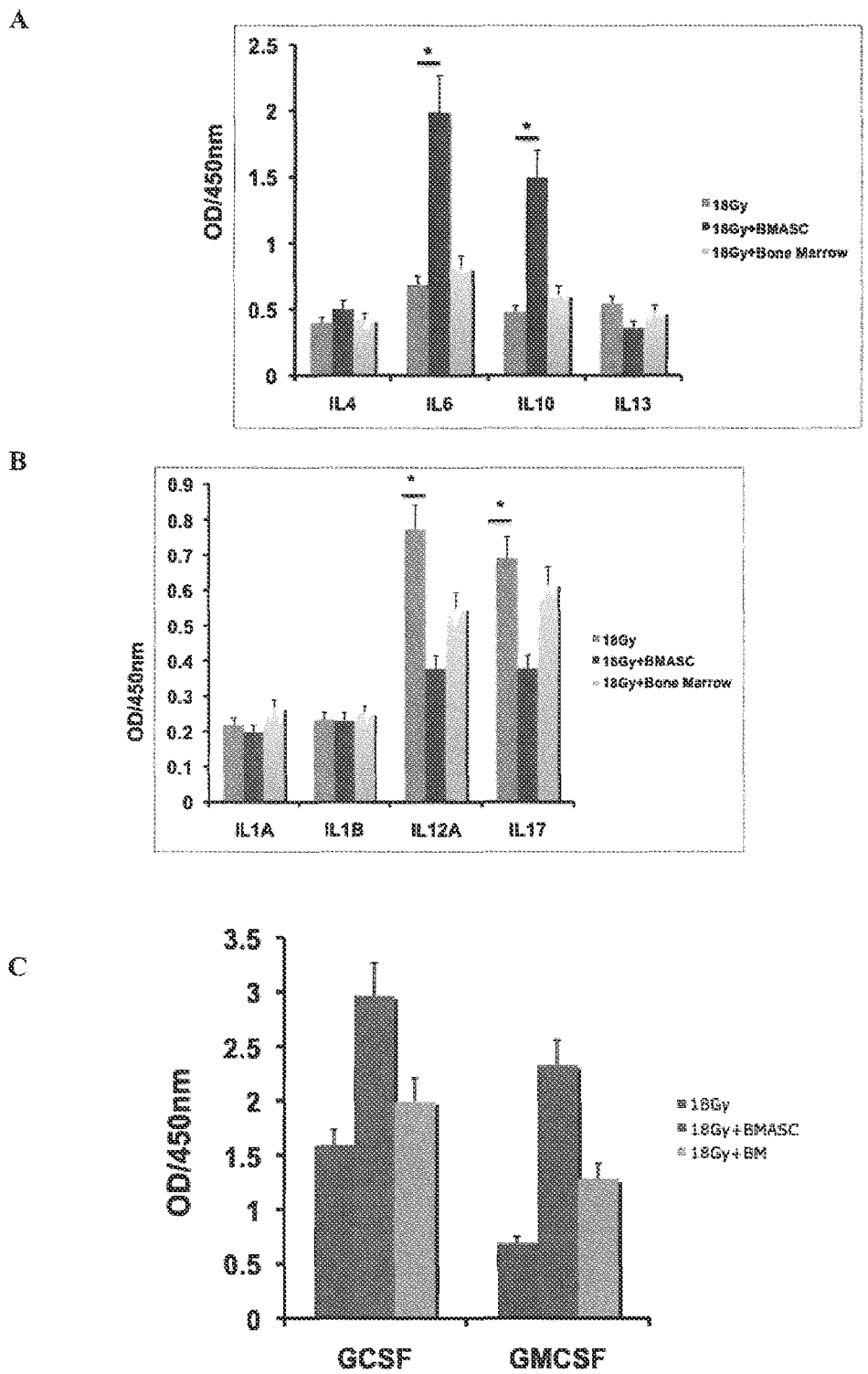
FIG. 18(A)-18(B). Multi cytokine ELISA. 18(A). Anti-inflammatory cytokines, IL6 (p<0.004) and IL10 (p<0.002) levels were significantly increased in the AIR+BMASCT-treated animals, compared to AIR alone. Induction of anti-inflammatory cytokine IL6 (p<0.007) and IL10 (p<0.005) was also observed in the animals treated with AIR+CD11b+ ve BMASCT. Transplantation of freshly isolated bone-marrow cells could not increase the anti-inflammatory cytokine level. 18(B). AIR+BMASCT reduces the pro-inflammatory cytokine levels (IL12A, IL17), compared to AIR alone. Transplantation of freshly isolated bone-marrow cells could not reduce the pro-inflammatory cytokine level compare to AIR alone. 18(C). AIR+BMASCT induces the GMCSF and GCSF levels compared to AIR alone. Transplantation of freshly isolated bone-marrow cells did not induce the GMCSF and GCSF level.
Figure 19:
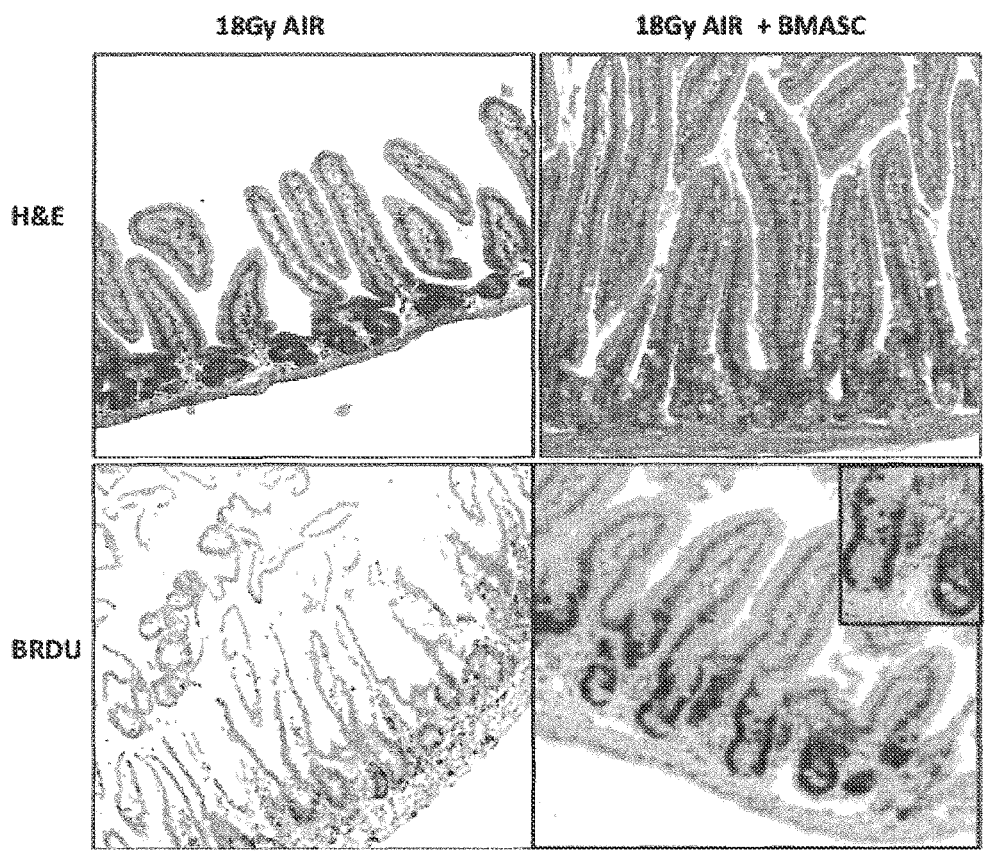
FIG. 19. BMSCT maintains villus length after radiation injury. Low magnification images (10×) of jejunal cross-sections showed the reduction of villi length and thickness (H&E staining) with the decrease in Brdu positive crypt cells in irradiated cohort (18 Gy AIR) compared to 18 Gy+BMASC group.

RIGS is associated with a systemic inflammatory response syndrome (SIRS) resulting from bacterial entry from the denuded gut lumen and resultant endotoxemia[26]. We performed multi-cytokine ELISA in the serum of animals that received AIR alone and compared them with those that received AIR+BMASCT. Compared to untreated controls, there was a significant increase in serum pro-inflammatory cytokines, such as, IL12A (p<0.001), IL17 (p<0.006) in animals that received AIR (FIG. 6(C)) or AIR+BMT (FIG. 18(B)). BMASCT reduced the secretion of these inflammatory cytokines, while inducing the release of anti-inflammatory cytokines, IL6 (p<0.004) and IL10 (p<0.002) (FIG. 6(B)) that may dampen the SIRS in RIGS. AIR+BMASCT also increased the levels of serum GCSF (p<0.006) and GMCSF (p<0.007) (FIG. 6(D)) compared to AIR alone, which could induce macrophage infiltration and activation in the irradiated intestine (FIG. 5(B)).

Since BMASCT was postulated to modulate the ISC niche, we also examined the expression of mRNA level of intestinal growth factors and inflammatory cytokines from cells isolated from the crypt region. Quantitative RT-PCR analysis of crypt cell mRNA from AIR+BMASCT-treated animals showed several fold increase in expression level of intestinal growth factors, such as, FGF10, KGF, EGF, FGF2, and anti-inflammatory cytokine, IL-10 with BMASCT at 24 hr post-AIR, compared to AIR alone (see Tables 1 and 2). While R-spondin1 levels were elevated in the serum, its expression was absent in the crypt region. In contrast to BMASCT, whole BMT had lower expression of intestinal survival and growth factors and chemokines, such as, EGF, FGF10, FGF, IGF1, VEGFa, CSF1, CXCL1 and CXCL12 (Table 1). These results suggested that bone marrow-derived stromal cells could modulate the regenerative signals in intestinal microenvironment.

TABLE 1 qPCR analysis of different growth factor mRNA level in intestinal crypt cells. RT + BMASCT treated group showed significant increase in mRNA level of growth factors compared to RT cohort.

| GROWTH FACTORS | RT + BMASCT VS RT log2(Fold Change) | RT + BM VS RT log2(Fold Change) |
| --- | --- | --- |
| EGF | 13.70 | −2.11 |
| FGF10 | 124.59 | −2.01 |
| FGF2 | 11.02 | 4.71 |
| KGF | 2.19 | 5.22 |
| IGF1 | 106.21 | −2.97 |
| HGF | 3.27 | 1.09 |
| VEGFa | 2.16 | −3. |
| CSF1 | 4.83 | −5.00 |
| CSF3 | 4.25 | 1.13 |
| CXCL1 | 28.34 | 2.04 |
| CXCL12 | 67.80 | −1.34 |

TABLE 2 qPCR analysis of inflammatory cytokine in intestinal crypt cells. RT + BMASCT treated group showed significant increase in mRNA level of anti-inflammatory cytokine level compared to RT cohort.

| CYTOKINE AND CYTOKINE RECEPTOR | BMASCT + RT VS RT log2(Fold Change) | RT + BM VS RT log2(Fold Change) |
|---|---|---|
| IL10 | 2.10 | 2.16 |
| IL10Ra | 2.32 | 2.02 |
| IL11 | 2.23 | −3.24 |

TABLE 3

Median survival time of animals exposed to 18Gy AIR and 10.4Gy WBI followed by cell transplantation. Please note the clear difference of median survival time of the animals exposed to 18Gy AIR compared to 10.4Gy WBI.

| | Median survival time (Days) | |
|---|---|---|
| Treatment | 18Gy AIR | 10.4 Gy WBI |
| IR | 6 ± 1.2 | 10 ± 1.4 |
| IR + GROWTH MEDIA | 6 ± 1.8 | 7 ± 1.1 |
| IR + BMNAC | 12 ± 1.6 | 7 ± 1.8 |
| IR + BM | 11 ± 1.2 | 10 ± 1.3 |

Figures 7A, 7B:
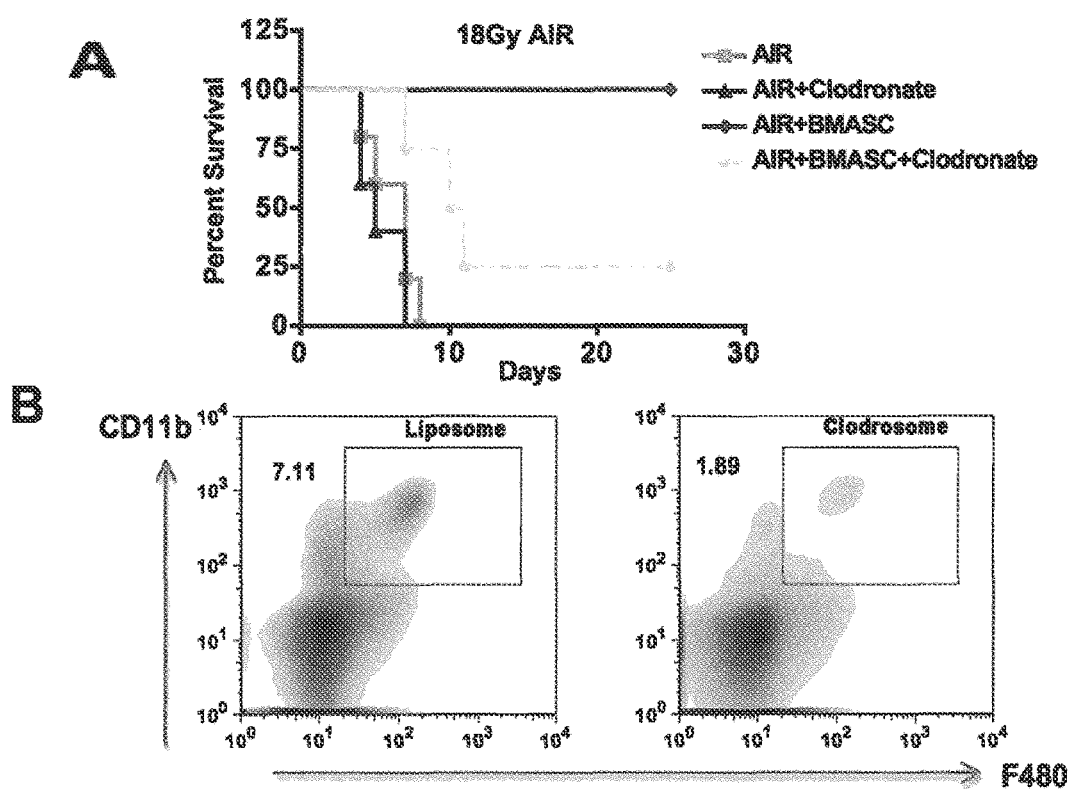
FIG. 7(A)-7(F). BMASCT promotes signaling cross-talk between macrophages and ISMEF in the ISC niche post-AIR. 7(A). Kaplan-Meier survival analysis of animals treated with AIR+BMASCT following depletion of host macrophages by clodrosome. Clodrosome treatment reduced the animal survival after AIR+BMASCT to 25%, indicating host macrophages are needed for mitigation. 7(B)-(C). Flow cytometric 7(B) and confocal microscopic evaluation 7(C) of macrophages. Note depletion of host macrophages post-AIR by clodrosome. 7(D)-(F). Inhibition of COX2 reduced the BMASCT mediated mitigation of FIG. 7(D). Kaplan-Meier survival analysis. Administration of COX2 inhibitor, NS398, reduced survival of animals treated with AIR+BMASCT (p<0.008). Survival was improved to 80% with dmPGE2 supplement. 7(E)-(F). TUNEL staining of crypts. AIR+BMASCT inhibited apoptosis in the crypts at day 3.5, which was increased by NS398-mediated COX2 inhibition (p<0.002). Supplementation with dmPGE2 restored the anti-apoptotic effect of BMASCT (p<0.005).
Figures 7C, 7D:
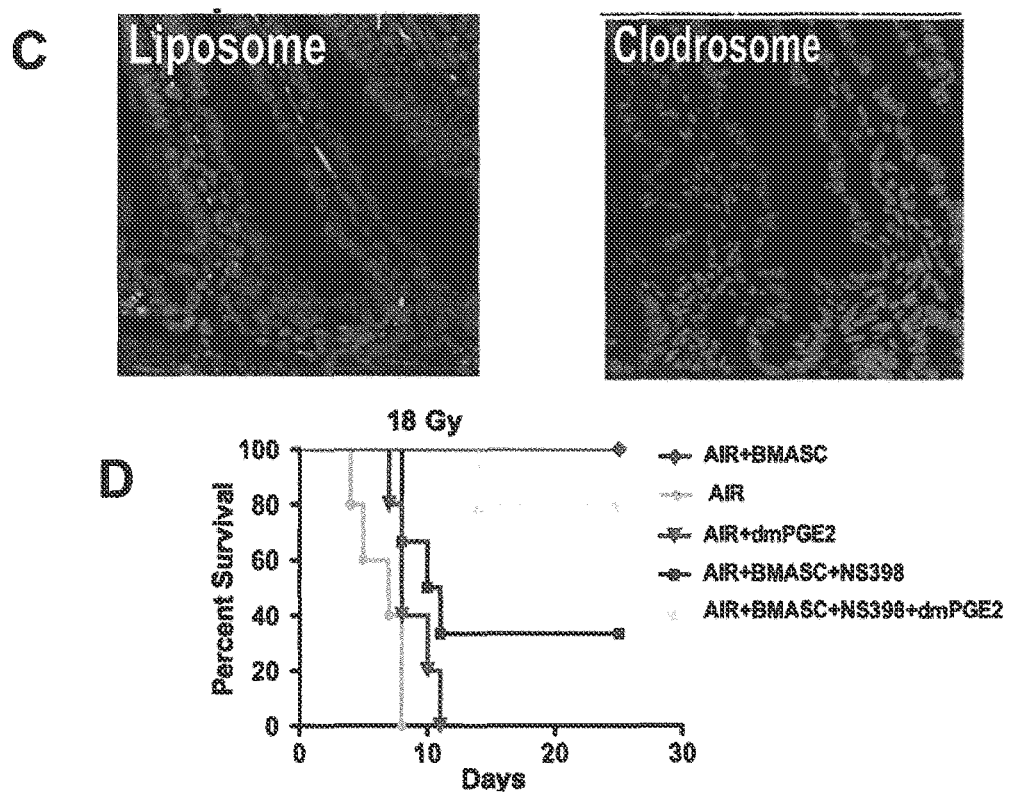

Depletion of host macrophages reduces survival of AIR+BMASCT-treated mice. Pericryptal macrophages play an important role in forming synapses with ISC and modulating ISC regeneration[6]. To evaluate the involvement of host macrophages in RIGS mitigation, we depleted them by administering clodronate-filled liposomes (clodrosome) intraperitoneally from day 4 pre-AIR to a week post-AIR. The depletion of macrophages (CD11b+F480+) was verified using FACS analysis of splenocytes and immunohistochemical staining of intestinal sections (FIG. 7B-C). Macrophage depletion reduced the RIGS-mitigating effect of BMASCT with only 25% of the animals surviving after 18 Gy AIR, compared to 100% survival in mice that received AIR+BMASCT (FIG. 7A). This indicated an essential role of host macrophages in the regenerative process of irradiated intestines.

Figures 7E, 7F:
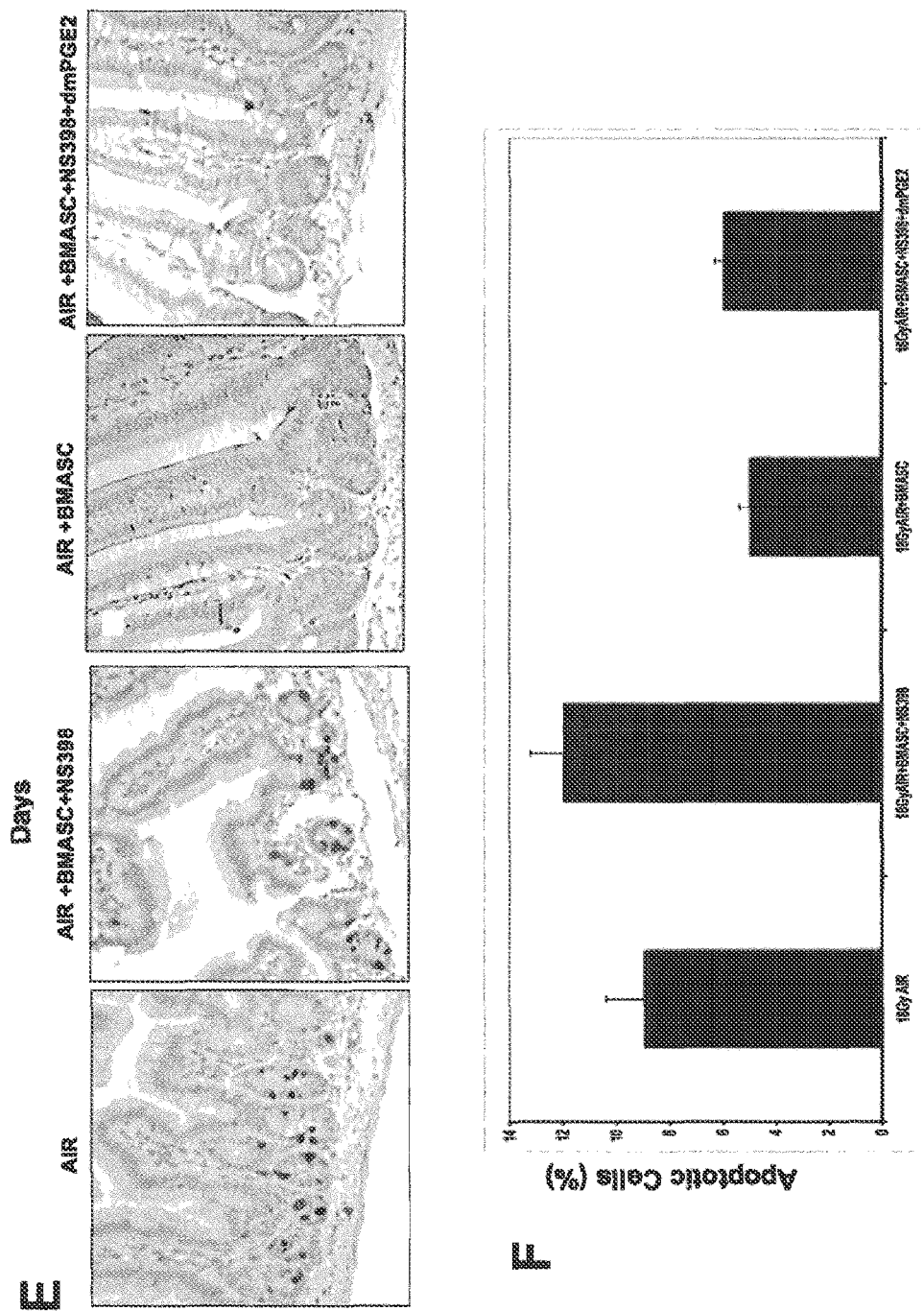

Prostaglandin E2 (PGE2) is an essential mediator for BMASCT-induced RIGS mitigation. Intestinal macrophages have been implicated in inducing the expression of COX2 for PGE2 synthesis by ISEMF. PGE2 reduces the radiation-induced apoptosis of intestinal crypt cells by binding to the EP receptor on ISC[9,10]. To further elaborate on the cross-talk of preicryptal macrophages and ISEMF in the ISC niche that are replenished after BMASCT, we inhibited PGE2 synthesis with COX2 inhibitor NS398. COX2 inhibition reduced the BMASCT-mediated survival of irradiated animals to 35% (p<0.008), which was restored to 80% with dmPGE2 supplementation (FIG. 7D). Tunnel staining demonstrated that COX2 inhibition significantly increased the percent of apoptotic cell in crypt of animals that received AIR+BMASCT (p<0.002) (FIG. 7(E)-7(F)), which was reduced with dmPGE2 supplementation (FIG. 7(E)-7(F)).

Discussion

This is the first demonstration of RIGS mitigation by BMASCT, 24 hours after exposure to high doses of either, whole body irradiation (10.4 Gy) or AIR (16-20 Gy). BMASCT restores the ISC niche, including, the pericryptal macrophages, endothelial cells and ISEMF. In contrast to BMT that mitigates radiation-induced hematopoietic syndrome by donor cell repopulation, BMASCT mitigates RIGS via accelerated regeneration of irradiated host ISC rather than its replacement with donor derived cells. This would require the presence of Lgr5+ ISCs, which were noted in crypt for 24 hrs post-AIR, thus affording a time window for effective radio-mitigation. Hence, BMASCT was successful in rescuing animals up to 24 hrs post-radiation but not at later time points.

Since the majority of the donor cells were lodged in the lungs, radiation injury was perhaps mitigated by secreted growth factors. Potential candidates include R-spondin1, KGF, FGF2, PDGF-B, IL-6, IL-10, G-CSF and GM-CSF. Serum R-spondin1 levels increased by 8-10-fold. Human R-spondin1, a 29 kd, 263 amino acid protein that acts as a specific growth factor of intestinal crypt cells[27], has been shown to be a mucosal protective agent in radiation and chemotherapy-induced mucositis[28]. It has been demonstrated that R-spondin1 can be radioprotective for RIGS[1]. R-spondin1 binds with high affinity to the Wnt co-receptor, LRP6, and induce phosphorylation, stabilization and nuclear translocation of cytosolic β-catenin, thereby activating TCF/β-catenin-dependent transcriptional responses in intestinal crypt cells[29]. The presence of nuclear β-catenin in the crypt cells of AIR+BMASCT-treated animals could represent R-spondin1-mediated Wnt activation in ISC of these animals. BMASCT also modulated the mRNA expression of several intestinal growth factors in the crypt cells of irradiated intestine. However, R-spondin1 was not expressed in the cells of the crypt region.

BMT can rescue animals that develop primarily a hematopoietic syndrome with exposure to radiation doses <8-9 Gy in single fraction. With higher doses of irradiation, intestinal injury sets in and animals cannot be rescued by BMT alone. Although, bone marrow-derived, MSCs contribute to intestinal regeneration and transplantation of these cells ameliorated intestinal injury in murine models of radiation and chemotherapy-induced injury, colitis, and autoimmune enteropathy[16,18,30,31], MSC transplantation alone failed to improve survival of animals exposed to higher irradiation doses (>9.6 Gy) in a single fraction[16, 17,18]. The present study shows that whole bone marrow transplantation cannot mitigate intestinal injury induced by irradiation (>10.4 Gy). However, upon expansion/amplification of stromal cells in mesenchymal basal medium culture, and transplantation of a combination of CD11b+ macrophages and CD11b− MSC and EPCs could effectively mitigate RIGS. Important differences were noted in the animals that received BMASCT from BMT. In contrast to the AIR+BMT cohort, the AIR+BMASCT cohorts had elevated levels of serum R-spondin1 and expressed various intestinal growth factors in the crypt cells, suggesting a role of stromal cells in secreting growth factors and signals for inducing ISC proliferation in these animals. These stromal cells secrete factors that support the regeneration of the ISC and its niche. Increased serum levels of PDGF-B and FGF2, growth factors for ISEMF and EPC proliferation[25], along with GMCSF and GCSF[32,33] for macrophage activation support the involvement of BMASC in restoring the ISC niche. Several growth factors that could mediate intestinal regeneration, such as, FGF10, FGF, EGF, IGF1, VEGFa, CSF1 and CXCL12 were induced in the crypt cells in BMASCT-transplanted animals. ISEMF residing throughout the lamina propria and pericryptal region plays a vital role in intestinal structural regeneration[7,8,25]. Similarly, submucosal macrophages are activated by the bacterial ligands for Toll-like receptors (TLR) upon bacterial entry through disrupted intestinal mucosa. Thus activated macrophages act as "mobile cellular transceivers" that transmit regenerative signals to ISCs[6]. Moreover, crosstalk between host macrophages and ISEMF was necessary for RIGS mitigation by PGE2-mediated inhibition of radiation-induced apoptosis of crypt cells, also noted in other studies[9,10].

In summary, these experiments point towards a new paradigm for RIGS mitigation, whereby growth factors secreted after BMASCT induce regeneration of the irradiated host crypt progenitors and ISC niche, thereby, accelerating functional recovery of the intestine in RIGS. By reducing the levels of pro-inflammatory cytokines, while inducing anti-inflammatory cytokines, BMASCT also dampens the SIRS in RIGS.

Materials and Methods

Animals

Five- to 6-weeks-old male C57Bl/6 (NCI—Fort Dietrich, Md.), dipeptidyl peptidase-deficient (DPPIV-ve) (gift from Dr. David Shafritz, Einstein College, Bronx, N.Y.) Lgr5-EGFP-IRES-creERT2 (Jackson Laboratories, Bar Harbor, Me.) mice were maintained ad libitum and all studies were performed under the guidelines and protocols of the Institutional Animal Care and Use Committee of the Albert Einstein College of Medicine.

Irradiation

Irradiation was performed on anesthetized mice (intraperitoneal ketamine and xylazine 7:1 mg/ml for 100 μl/mouse) using a 320 KvP, Phillips MGC-40 Orthovoltage irradiator at a 50 cm SSD with a 2 mm copper filter at a dose rate of 72 cGy/min. WBI (10.4 Gy) was administered or escalating doses of whole AIR (16-20 Gy) after shielding the thorax, head and neck and extremities and protecting a significant portion of the bone marrow, thus inducing predominantly RIGS.

BMASC Transplantation

Donor bone marrow cells were harvested using sterile techniques from the long bones from C57Bl/6 mice and cultured in mesenchymal stem cell (MSC) basal medium (Cambrex-Lonza, Walkersville, Md.) supplemented with 10% heat inactivated FBS, 1% Glutamine, and 1% Penicillin/Streptomycin for 4 days, followed by collection of adherent cells as BMASC. BMASC were then subjected to flow cytometric characterization to determine the percentage of MSC (CD105+CD45−/CD29+CD45−), endothelial progenitor cell (EPC) (CD34+CD133+CD45−) and macrophages (CD11b+ F480+). CD11b+ve and CD11b−ve cells were fractionated using anti-CD11b-magnetic beads (MACS, Miltenyi Biotec, Auburn, Calif.), following the manufacturer's protocol. Fractionated and whole BMASC (2×106 cells/mice) were injected intravenously via tail vein to C57Bl6 mice at 24 and 72 s hours after irradiation.

Characterization of RIGS

Animals were sacrificed at 1, 3.5 and 7 days after irradiation for histopathological analysis to examine apoptosis by TUNEL staining, regenerating crypt colonies and villi denudation (Hematoxylin and eosin staining)[1]. To visualize villous cell proliferation, each mouse was injected intraperitoneally with 120 mg/kg BrdU (Sigma-Aldrich, USA) 2-4 hrs prior to sacrifice and mid-jejunum was harvested for paraffin embedding and BrdU immunohistochemistry (Supplement). The crypt proliferation rate was calculated as the percentage of BrdU positive cells over the total number of cells in each crypt. A total of 30 crypts were examined per animal for all histological parameters. A regenerative crypt was confirmed by immunohistochemical detection of BrdU incorporation into five or more epithelial cells within each crypt, scored in a minimum of four cross-sections per mouse. The number of regenerative crypts was counted for each dose of irradiation and represented using the crypt microcolony assay [1,21,22].

Characterization of ISC

Lgr5+ve ISCs were detected in 4% para-formaldehyde-fixed sections from Lgr5-EGFP-ires-CreERT2 mouse jejunum by examining EGFP expression using confocal microscopy, according to published protcols[3]. GFP expression was also measured by flow cytometry of crypt cells, isolated from Lgr5-EGFP-ires-CreERT2 mouse intestines, according to method described earlier [23].

Characterization of ISC Niche

ISEMF were stained in formalin-fixed, paraffin-embedded tissue sections for alpha-smooth muscle actin ($\alpha$-SMA) and desmin using Cy3-conjugated mouse anti-a-SMA (1:500; Sigma, St. Louis, Mo.) and rabbit anti-desmin (1:250; Abcam, Cambridge Mass.) antibody, respectively, with overnight incubation at 4° C. followed by staining with goat anti-rabbit Alexafluor 488 (1:1000; Molecular Probes, Carlsbad, Calif.). Pericryptal macrophages were stained by AlexaFluor488-conjugated, rat, anti-mouse, F480 antibody (1:50; Caltag laboratories, Carlsbad, Calif.). Images were captured using a Zeiss SP2 confocal microscope at 63× optical zoom and the macrophages were counted by using the VelocitySoft Version 5.0 (Improvision, Waltham, Mass.) in 10 fields per mice in various cohorts (n=3).

Intestinal Absorption

Functional regeneration of the irradiated intestines were determined by measuring intestinal absorption by a xylose uptake assay[1,34]. Briefly, 5% w/v D-xylose solution was administered orally by feeding tube (100 mL/mice, n=5/cohort), followed by collection of blood 2 hours post-feeding. Plasma xylose levels were measured by a modified micromethod [34].

Cytokines and Growth Factors in Blood

Intestinal growth factors, R-spondin1, keratinocyte growth factor (KGF), basic fibroblast growth factor (bFGF) and platelet derived growth factor-b (PDGFb) were detected in serum by immunoblotting using goat polyclonal anti-mouse antibodies to R-spondin1 (1:200; R & D Systems, Minneapolis, Minn.), KGF (1:250), bFGF (1:250) and PDGFb (1:250). Inflammatory cytokines were measured in the serum by ELISA, using a multianalyte ELISArray kit (SA Biosciences, Fredrick, Md.), according to manufacturer's protocol.

Cytokine and Growth Factors in Crypt Cells

To compare the mRNA levels of different growth factors and cytokines in intestine crypt cells from AIR and AIR+BMASCT treated mice, real time PCR were performed using growth factor (cat #PAMM-041) and cytokine (cat #PAMM-011) real time array system from SA Biosciences.

Macrophage Depletion

To deplete macrophages liposomal clodronate (Encapsula NanoSciences, Nashville, Tenn., USA) (30 mg/kg of body weight) was injected intravenously from day 4 pre-AIR to a week post-AIR. Plain liposome was injected as control. Neither the clodronate filled nor the empty liposomes are considered toxic to the organs.

Inhibition of COX2

NS-398 (Biomol, Plymouth Meeting, Pa.) was administered at a dose of 1 mg/kg of body weight (3×/week, ip) started at 1 week prior to AIR. Animals treated with dmPGE2 (Sigma) received a dose of 0.5 mg/kg of body weight (3×/week, ip) started at 1 week prior to AIR.

Kaplan-Meier Survival Analysis

Mice survival/mortality in different treatment group was analyzed by kaplan-Meier as a function of radiation dose using Sigma-Plot and Graphpad Prism-4.0 software for Mac.

Statistical Analysis of Digital Images

Sampling regions were chosen at random for digital acquisition for data quantitation. Digital image data was evaluated in a blinded fashion as to any treatment. A two-sided student's t-test was used to determine significant differences between experimental cohorts (P<0.05) with representative standard errors of the mean (SEM).

BMASC Characterization.

For characterization of mesenchymal stem cell, single cell suspensions of BMASCs were stained with CD105 conjugated with PE (BD Biosciences, San Diego, Calif.) and CD45 conjugated with FITC (BD Biosciences). To determine the EPC population, BMASCs were stained with CD34 (pacific blue) (Ebioscience, San Diego, Calif.) CD45 (FITC) CD133 (APC) (Ebioscience). For determination of monocyte/macrophage population BMASC were stained with CD11b (PE) (BD Biosciences) and F480 (FITC) (BD Biosciences). BMASC were acquired with the LSRII flow cytometer (BD Biosciences). The acquired data was analyzed with FlowJo v. 7.1 (Treestar Inc, Ashland, Oreg., USA) software.

Macrophage Depletion from BMASC.

CD11b+ve, macrophages were depleted from BMASC using anti-CD11b-magnetic beads (MACS, Miltenyi Biotec, Auburn, Calif.), following the manufacturer's protocol. Briefly, BMASC were incubated with CD11b micobeads for 15 mins at 4-8° C. Then cell suspension was washed by adding 10× labeling volume of buffer per $10^8$ cells and centrifuged at 300×g for 10 mins. Supernatant was pipette off and 500 µl buffer was added per $10^8$ cells. Then MS magnetic column (Miltenyl Biotec) was placed in MACs separator (magnet) and prepared by rinsing the column with 500 µl of rinsing buffer. Cell suspension was applied onto the column. Unlabelled cells [CD11b–ve] were passed and collected in the flow through. Column was washed three times with 500 µl of buffer. Column was then removed from the magnetic field and placed in a suitable collection tube. 1 ml of buffer was added in the column and immediately flushed with plunger supplied with the column to separate the magnetically labeled cells from the column. CD11b positive and negative population was confirmed by flowcytometry using anti CD11b antibody (Miltenyl Biotec).

Histology.

The intestine of each animal was dissected, washed in PBS to remove intestinal contents and the jejunum was fixed in 10% neutral buffered formalin prior to paraffin embedding. Paraffin embedded tissue was processed and cut into 5 µm sections for hematoxylin and eosin and immunohistochemical staining. All hemotoxylin and eosin (Fisher Scientific, Pittsburgh, Pa.) staining was performed at the Histology and Comparative Pathology Facility in the Albert Einstein Cancer Center.

BrdU Immunohistochemistry & Measurement of Crypt Proliferation Rate.

Mouse was injected intraperitoneally with 120 mg/kg BrdU (Sigma-Aldrich, USA) 2-4 hrs prior to sacrifice and mid-jejunum was harvested for paraffin embedding and BrdU immunohistochemistry. Tissue sections were routinely deparaffinized and rehydrated through graded alcohols and incubated overnight at room temperature with a biotinylated monoclonal BrdU antibody (Zymed, South Francisco, Calif.). Nuclear staining was visualized using Streptavidin-peroxidase and diaminobenzidine (DAB) and samples were lightly counterstained with hematoxylin. Jejunum from mice, not treated with BrdU, was used as a negative control. Murine crypts were identified histologically as reported earlier[3]. High (400-600×) magnification digital photographs of crypts were taken at (Zeiss AxioHOME microscope) and crypt epithelial cells (paneth and non-paneth) intestinal sections were examined using ImageJ software. Cells with brown-stained nuclei from DAB staining were classified as BrdU positive. The crypt proliferation rate was calculated as the percentage of BrdU positive cells over the total number of cells in each crypt.

Immunohistochemistry.

For immunohistochemical staining of formalin-fixed, paraffin-embedded tissue sections, endogenous peroxidase activity was blocked for 30 min with methanol containing 0.3% $H_2O_2$. Antigen retrieval was performed by heating slides in pH 6.0 citrate buffer at 100° C. for 20 min in a microwave oven at 500 watts. Non-specific antibody binding was blocked for 20 minutes by incubation with serum free protein block (Dako, San Antonio, Calif.). Sections were further incubated with target specific primary and fluorescent conjugated secondary antibodies. Images were captured using a Zeiss (Thornwood, N.Y.) SP2 confocal microscope equipped with cooled CCD cameras at 63 optical zoom. Resolution of the images were same for both experimental and control groups.

Crypt Isolation.

In brief, isolated mouse small intestines were chopped into around 5 mm pieces and washed with cold PBS. The tissue fragments were incubated in 2 mM EDTA with PBS for 30 min on ice followed by centrifugation. After removal of EDTA medium, the tissue fragments were vigorously suspended by using a 10-ml pipette with cold PBS and fractionated thereafter by centrifugation to get the crypt-enriched sediment. The crypt-enriched fraction was further suspended with PBS with vigorous dispersions and subjected to centrifugation. The supernatant enriched with crypts were collected and passed through a 70-mm cell strainer (BD Bioscience) to remove residual villous material. Isolated crypts were centrifuged at 150-200 g for 3 min to separate crypts from single cells. Isolated crypts were incubated in culture medium for 45 min at 37° C., followed by trituration with a glass pipette. Dissociated cells were passed through cell strainer with a pore size of 20 mm and were acquired with the LSRII flow cytometer (BD Biosciences). The acquired data was analyzed with FlowJo v. 7.1 (Treestar Inc, Ashlaand, Oreg., USA) software.

Xylose Absorption Assay.

Xylose uptake assay among different treatment group (n=5/group) was performed, at various time points (1, 3.5, 7 and 10 days) after irradiation. A 5% w/v solution of D-xylose (100 µl/mouse) in deionized water was given orally by feeding tube and animals were sacrificed at 2 hrs post administration of D-xylose. Blood samples were collected in heparinized blood collection tubes (BD Biosciences, San Jose, Calif.). 50 µL of serum sample was added to 5 ml of phloroglucinol (1,3,5-trihydroxybenzene, Sigma Chemical Co., St. Louis, Miss.) color reagent (0.5 g of phloroglucinol, 100 ml glacial acetic acid and 10 mL of conc. HCL) heated to 100° C. in a water bath for 4 min to allow optimum color development. After equilibration to room temperature, sample absorption was determined with the aid of a spectrophotometer set at a wavelength of 554 nm.

Detection of Transplanted BMASC.

DPPIV deficient mice received AIR. The BMASC were transplanted as mentioned earlier. Frozen sections were prepared by freezing tissue in OCT (Tissue Tek) To analyze the engraftment of DPPIV positive transplanted cells in situ 5 uM cryostat sections were incubated with streptavidin conjugated anti mouse DPPIV (R&D systems, McKinley Place NE, Minneapolis) for overnight at 40 C and followed by incubation with streptavidin alexafluor 488. The nucleus was stained with DAPI. Images were captured using a Zeiss SP2 confocal microscope equipped with cooled CCD cameras at 63 optical zoom. The DPPIV positive cells were counted by using velocity soft version 5 (Improvision). Based on the intensities, number of cells were determined by scoring at least 10 fields from each animal (n=3). Resolution of the images were same for both experimental and control groups.

Immunoblotting of Serum R-Spondin1, KGF, FGFb, PDGFb.

Blood was drawn from the retro-orbital plexus and serum was isolated by centrifugation at 10,000 rpm for 5 min. Serum protein concentration was determined by Bradford assay kit (Bio-Rad Laboratories, Hercules, Calif.). Approximately 100 µg of protein was subjected to 14% SDS-PAGE, followed by electroblotting onto polyvinylidene difluoride membranes. The blot was blocked with 5% skim milk in Tris-buffered saline (10 mM Tris-HCl (pH 7.4), 150 mM NaCl, 0.05% Tween 20) followed by incubation with primary antibody (1:200 dilution), goat polyclonal anti mouse R-spondin1 (R & D Systems, Minneapolis, Minn.), KGF (1:250), FGFb (1:250), PDGFb (1:250) and then with secondary antibody (1:500 dilution), horseradish peroxidase (HRP) conjugated bovine anti-goat antibody (Santa-Cruz Biotechnology, Inc., Santa Cruz, Calif.). The blots were developed using Enhanced Chemiluminence assay (Amersham Pharmacia Biotech, Inc, Piscataway, N.J.).

ELISA Array of Inflammatory Cytokines.

Blood was drawn from the retro-orbital plexus and serum was isolated by centrifugation at 10,000 rpm for 5 min. Serum protein concentration was determined by Bradford assay kit (Bio-Rad Laboratories, Hercules, Calif.). Approximately 100 µg of serum protein was subjected for ELSA using multianalyte ELISArray kit (SA Biosciences, Fredrick, Md.) according to manufacturer's protocol.

Isolation of Cells Along the Crypt-Villus Axis.

Cells along the crypt-villus axis was isolated following the protocol described by Chang et al [1] and Ferraris et al [2]. Briefly the entire small intestine (duodenum to terminal ileum) was removed and flushed once with phosphate buffered saline (PBS). The small intestine was then tied off at one end, and filled to distension with PBS prior to closing the open end followed by incubation at 37° C. for 15 minutes in 15 ml of buffer B (96 mM NaCl, 1.5 mM KCl, 27 mM Na-citrate, 8 mM $KH_2PO_4$, and 5.6 mM $Na_2HPO_4$, pH 7.3), and for 10 minutes in 15 ml of buffer C (PBS plus 1.5 mM EDTA, 0.5 mM dithiothreitol, and 1 mg/ml bovine serum albumin), in a shaking 37° C. incubator. Detached enterocytes were collected (Fraction 1) at the end of 15 minutes incubation and 15 ml of fresh buffer C added to the tissue. This procedure was repeated four more times, the steps lasting 25, 25, 25 and 30 minutes, respectively (Fractions 2, 3, 4 and 5), for a total of 120 minutes of incubation time. Viability and morphology of isolated cells were identified by trypan blue using light microscopy. Fractions 3-5 were further subjected to RNA isolation as they are reportedly known to contain crypt region.

RNA Isolation and cDNA Synthesis.

Isolated crypt cells were lysed using RLT buffer from RNeasy Mini Kit (Qiagen, Valencia, Calif.) and 1% beta-mercaptoethanol mix. Qiagen's protocol for the RNeasy Mini Kit with on-column DNA digestion was used to isolate RNA from the lysates. Isolated RNA samples were subjected to cDNA synthesis using first strand synthesis kit from SA Biosciences (Frederick, Md.) and according to manufacturer protocol and stored at −80° C. prior to use until further use for real time PCR.

2. Adipose Derived Non-Adherent Stromal Cells

The transplantation of adipose tissue-derived stromal cells (ADSC) containing a unique mixture of mesenchymal progenitor cells (MSC), endothelial progenitor cells (EPC) and macrophages was examined as to its effect in mitigating RIGS.

Figure 8:
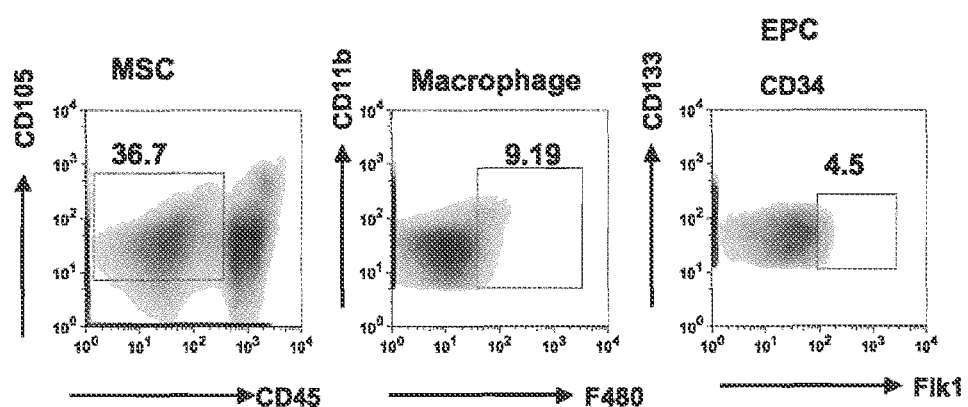
FIG. 8. Flow cytometric determination of mesenchymal stem cell (CD105+CD45−), epithelial progenitor cell (CD133+ CD34+ Flk+) and myeloid/macrophage (CD11b+ F480+) population in ADNASC.

Donor adipocytes were harvested from C57Bl/6 mice subcutaneous fat using sterile techniques and were cultured in in DMEM with 10% FBS and 1% PEN-STREP for 4 days. Non-adherent cells present in culture supernatant were collected by centrifugation and resuspended in PBS prior to intravenous transplantation. C57Bl/6 mice received a single fraction of whole body irradiation (WBI; 8-10.4 Gy) followed by transplantation of ADNASC ($10^6$ cells/mice) 24 hours after exposure to IR via tail vein injection. Culture supernatant and adipose-derived adherent cells (ADAC) were also administered to the mice at 24 hr post irradiation. Irradiated controls received culture medium. Flow cytometry demonstrated 36.7%±1.8 MSC (CD105+CD45−), 4.5%±2.3 EPC (CD133+ CD34+ Flk+) and 9.19%±1.7 myeloid/macrophages (CD11b+ F480+) in ADNASC donor cells (FIG. 8).

Figure 9:
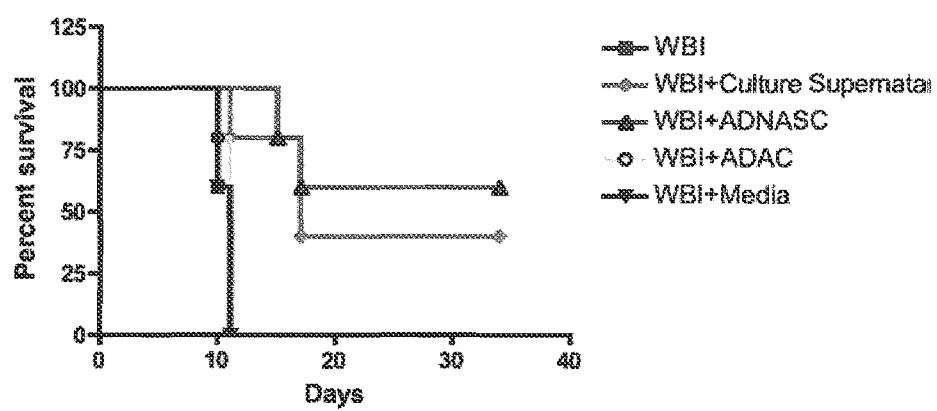
FIG. 9. ADNASC transplantation mitigates RIGS and improved survival of C57Bl/6 mice from radiation-induced mortality. Kaplan-Meier survival analysis of mice receiving ADNASC transplantation 24 hrs after 10.4 WBI Note 60% survival of mice receiving ADNASC and 40% survival of mice receiving culture supernatant, despite exposure to lethal dose of 10.4 Gy WBI. ADAC transplant and administration of media failed to rescue mice from irradiation lethality.
Figures 10A, 10B, 10C, 10D:
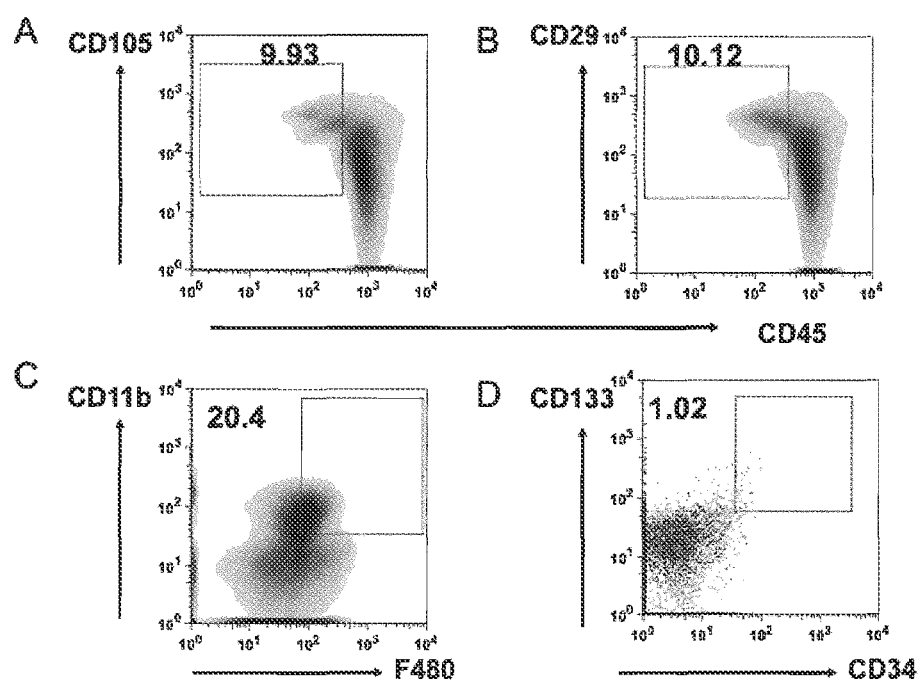
FIG. 10(A)-(D). Flowcytometric characterization of freshly isolated bonemarrow cells for expression of MSC specific (A) (CD105+CD45−) (B) (CD29+CD45), (C) macrophage specific (CD11b+F480+) and (D) EPC specific (CD133+CD34+CD45−) markers. It was noted that bone marrow cell were primarily enriched with CD45+ hematopoetic cells (A-B).

FIG. 9 demonstrates that 60% of the mice that received ADNASC transplantation and 40% of mice that received culture supernatant survived a lethal dose of WBI (10.4 Gy) while 100% of the controls that received WBI, WBI+ADAC and WBI+culture medium died within 12 days (p<0.003 and p<0.01 respectively in Kaplan-Meier analysis). Since the animals survived >30 days after exposure to 10.4 Gy of WBI, ADNASC transplantation mitigated the effects of RIGS and radiation-induced hematopoeitic syndrome. Transplantation of adipose-derived adherent cells could not rescue the animals from RIGS (FIG. 2). In conclusion, this is the first demonstration that transplantation of adnasc could mitigate RIGS after exposure to lethal doses of IR.

The present study has shown for the first time that ADSC transplantation (ADSCT) and/or ADSC culture supernatant can mitigate RIGS, when administered even after 24 hrs of lethal doses of irradiation (10.4 Gy WBI). This is the first demonstration of mitigation for RIGS with adipose-derived cell therapy. ADSC is an attractive option for therapy due to easy accessibility and large number of cosmetic liposuction procedures that are routinely performed. Remarkably, this effect was seen even when ADSCT was administered 24 hrs after radiation exposure, making this therapy a desirable radiation countermeasure candidate.

REFERENCES

1. Bhanja P, Saha S, Kabarriti R, Liu L, Roy-Chowdhury N, et al. (2009) Protective role of R-spondin1, an intestinal stem cell growth factor, against radiation-induced gastrointestinal syndrome in mice. PLoS One 4: e8014.
2. Potten C S, Booth C, Pritchard D M (1997) The intestinal epithelial stem cell: the mucosal governor. Int J Exp Pathol 78: 219-243.
3. Barker N, van Es J H, Kuipers J, Kujala P, van den Born M, et al. (2007) Identification of stem cells in small intestine and colon by marker gene Lgr5. Nature 449: 1003-1007.

4. Paris F, Fuks Z, Kang A, Capodieci P, Juan G, et al. (2001) Endothelial apoptosis as the primary lesion initiating intestinal radiation damage in mice. Science 293: 293-297.
5. Mills J C, Gordon J I (2001) The intestinal stem cell niche: there grows the neighborhood. Proc Natl Acad Sci USA 98: 12334-12336.
6. Pull S L, Doherty J M, Mills J C, Gordon J I, Stappenbeck T S (2005) Activated macrophages are an adaptive element of the colonic epithelial progenitor niche necessary for regenerative responses to injury. Proc Natl Acad Sci USA 102: 99-104.
7. Brittan M, Hunt T, Jeffery R, Poulsom R, Forbes S J, et al. (2002) Bone marrow derivation of pericryptal myofibroblasts in the mouse and human small intestine and colon. Gut 50: 752-757.
8. Brittan M, Wright N A (2002) Gastrointestinal stem cells. J Pathol 197: 492-509.
9. Riehl T, Cohn S, Tessner T, Schloemann S, Stenson W F (2000) Lipopolysaccharide is radioprotective in the mouse intestine through a prostaglandin-mediated mechanism. Gastroenterology 118: 1106-1116.
10. Stenson W F (2004) Prostaglandins and the epithelial response to radiation injury in the intestine. Curr Opin Gastroenterol 20: 61-64.
11. Okamoto R, Yajima T, Yamazaki M, Kanai T, Mukai M, et al. (2002) Damaged epithelia regenerated by bone marrow-derived cells in the human gastrointestinal tract. Nat Med 8: 1011-1017.
12. Brittan M, Chance V, Elia G, Poulsom R, Alison M R, et al. (2005) A regenerative role for bone marrow following experimental colitis: contribution to neovasculogenesis and myofibroblasts. Gastroenterology 128: 1984-1995.
13. Gregory C A, Prockop D J, Spees J L (2005) Non-hematopoietic bone marrow stem cells: molecular control of expansion and differentiation. Exp Cell Res 306: 330-335.
14. Le Blanc K, Rasmusson I, Sundberg B, Gotherstrom C, Hassan M, et al. (2004) Treatment of severe acute graft-versus-host disease with third party haploidentical mesenchymal stem cells. Lancet 363: 1439-1441.
15. Nemeth K, Leelahavanichkul A, Yuen P S, Mayer B, Parmelee A, et al. (2009) Bone marrow stromal cells attenuate sepsis via prostaglandin E(2)-dependent reprogramming of host macrophages to increase their interleukin-10 production. Nat Med 15: 42-49.
16. Semont A, Mouiseddine M, Francois A, Demarquay C, Mathieu N, et al. (2010) Mesenchymal stem cells improve small intestinal integrity through regulation of endogenous epithelial cell homeostasis. Cell Death Differ 17: 952-961.
17. Abdel-Mageed A S, Senagore A J, Pietryga D W, Connors R H, Giambernardi T A, et al. (2009) Intravenous administration of mesenchymal stem cells genetically modified with extracellular superoxide dismutase improves survival in irradiated mice. Blood 113: 1201-1203.
18. Zhang J, Gong J F, Zhang W, Zhu W M, Li J S (2008) Effects of transplanted bone marrow mesenchymal stem cells on the irradiated intestine of mice. J Biomed Sci 15: 585-594.
19. Mason K A, Withers H R, McBride W H, Davis C A, Smathers J B (1989) Comparison of the gastrointestinal syndrome after total-body or total-abdominal irradiation. Radiat Res 117: 480-488.
20. Terry N H, Travis E L (1989) The influence of bone marrow depletion on intestinal radiation damage. Int J Radiat Oncol Biol Phys 17: 569-573.
21. Potten C S (1990) A comprehensive study of the radiobiological response of the murine (BDF1) small intestine. Int J Radiat Biol 58: 925-973.
22. Withers H R, Elkind M M (1970) Microcolony survival assay for cells of mouse intestinal mucosa exposed to radiation. Int J Radiat Biol Relat Stud Phys Chem Med 17: 261-267.
23. Sato T, Vries R G, Snippert H J, van de Wetering M, Barker N, et al. (2009) Single Lgr5 stem cells build crypt-villus structures in vitro without a mesenchymal niche. Nature 459: 262-265.
24. Khan W B, Shui C, Ning S, Knox S J (1997) Enhancement of murine intestinal stem cell survival after irradiation by keratinocyte growth factor. Radiat Res 148: 248-253.
25. Powell D W, Mifflin R C, Valentich J D, Crowe S E, Saada J I, et al. (1999) Myofibroblasts. I I. Intestinal subepithelial myofibroblasts. Am J Physiol 277: C183-201.
26. Geraci J P, Jackson K L, Mariano M S (1985) The intestinal radiation syndrome: sepsis and endotoxin. Radiat Res 101: 442-450.
27. Kim K A, Kakitani M, Zhao J, Oshima T, Tang T, et al. (2005) Mitogenic influence of human R-spondin1 on the intestinal epithelium. Science 309: 1256-1259.
28. Zhao J, Kim K A, De Vera J, Palencia S, Wagle M, et al. (2009) R-Spondin1 protects mice from chemotherapy or radiation-induced oral mucositis through the canonical Wnt/beta-catenin pathway. Proc Natl Acad Sci USA 106: 2331-2336.
29. Binnerts M E, Kim K A, Bright J M, Patel S M, Tran K, et al. (2007) R-Spondin1 regulates Wnt signaling by inhibiting internalization of LRP6. Proc Natl Acad Sci USA 104: 14700-14705.
30. Parekkadan B, Tilles A W, Yarmush M L (2008) Bone marrow-derived mesenchymal stem cells ameliorate autoimmune enteropathy independently of regulatory T cells. Stem Cells 26: 1913-1919.
31. Tanaka F, Tominaga K, Ochi M, Tanigawa T, Watanabe T, et al. (2008) Exogenous administration of mesenchymal stem cells ameliorates dextran sulfate sodium-induced colitis via anti-inflammatory action in damaged tissue in rats. Life Sci 83: 771-779.
32. Ghia J E, Galeazzi F, Ford D C, Hogaboam C M, Vallance B A, et al. (2008) Role of M-CSF-dependent macrophages in colitis is driven by the nature of the inflammatory stimulus. Am J Physiol Gastrointest Liver Physiol 294: G770-777.
33. Heidenreich S, Gong J H, Schmidt A, Nain M, Gemsa D (1989) Macrophage activation by granulocyte/macrophage colony-stimulating factor. Priming for enhanced release of tumor necrosis factor-alpha and prostaglandin E2. J Immunol 143: 1198-1205.
34. Eberts T J, Sample R H, Glick M R, Ellis G H (1979) A simplified, colorimetric micromethod for xylose in serum or urine, with phloroglucinol. Clin Chem 25: 1440-1443.

What is claimed is:
1. A method of treating, mitigating, or protecting from, an injury associated with exposure of a subject to >10 Gy radiation comprising administering to the subject before, during or after exposure of the subject to the radiation an amount of a supernatant obtained from a culture of adipose tissue-derived adherent and non-adherent stromal cells, effective to treat, mitigate or protect from an injury associated with exposure of a subject to radiation.

2. The method of claim 1, wherein the radiation is gamma radiation.

3. The method of claim 1, wherein the supernatant obtained from a culture of adipose-derived stromal cells is administered to the subject prior to the exposure of the subject to the radiation.

4. The method of claim 1, wherein the supernatant obtained from a culture of adipose-derived stromal cells is administered to the subject subsequent to the exposure of the subject to the radiation.

5. The method of claim 1, wherein the culture conditions comprise a basal medium.

6. The method of claim 1, wherein the supernatant is administered by infusion into the subject.

7. The method of claim 1, further comprising obtaining the adipose-derived stromal cells from the subject prior to culturing them.

8. The method of claim 1, further comprising administering CD11b+ F480+ macrophages to the subject.

9. The method of claim 1, wherein the supernatant is administered to the subject less than 72 hours after exposure to the radiation.

10. The method of claim 9, wherein the supernatant is administered to the subject after 24 hours after the end of exposure, but less than 72 hours after the end of exposure, to the radiation.

11. A method of increasing the survival rate of a plurality of subjects exposed to an otherwise lethal dose of radiation comprising administering to each of the subjects before, during or after exposure of subjects to the otherwise lethal dose of radiation an amount of a supernatant obtained from a culture of adipose tissue-derived adherent and non-adherent stromal cells, effective to increase the survival rate of a plurality of subjects exposed to the otherwise lethal dose of radiation.

12. The method of claim 1, wherein the injury is radiation-induced gastrointestinal syndrome (RIGS).

* * * * *

UNITED STATES PATENT AND TRADEMARK OFFICE
CERTIFICATE OF CORRECTION

PATENT NO. : 9,782,441 B2
APPLICATION NO. : 14/131776
DATED : October 10, 2017
INVENTOR(S) : Chandan Guha et al.

Page 1 of 1

It is certified that error appears in the above-identified patent and that said Letters Patent is hereby corrected as shown below:

In the Specification

In Column 1, at Line 23, "This invention was made with government support under grant numbers 1RC2 AI087612-01 and 1U19AI091175-01 awarded by the National Institute of Allergy and Infectious Diseases. The government has certain rights in the invention." should read --This invention was made with government support under grant numbers AI087612 and AI091175 awarded by the National Institutes of Health. The government has certain rights in the invention.--

Signed and Sealed this
Twelfth Day of February, 2019

Andrei Iancu
*Director of the United States Patent and Trademark Office*